United States Patent
Elgena et al.

(10) Patent No.: US 11,638,572 B2
(45) Date of Patent: May 2, 2023

(54) METHODS AND APPARATUS FOR PERFORMING MEASUREMENTS ON AN ULTRASOUND IMAGE

(71) Applicant: BFLY Operations, Inc., Guilford, CT (US)

(72) Inventors: David Elgena, Orlando, FL (US); Matthew de Jonge, Brooklyn, NY (US); Cristina Shin, San Francisco, CA (US)

(73) Assignee: BFLY OPERATIONS, INC, Burlington, MA (US)

( * ) Notice: Subject to any disclaimer, the term of this patent is extended or adjusted under 35 U.S.C. 154(b) by 315 days.

(21) Appl. No.: 16/662,288

(22) Filed: Oct. 24, 2019

(65) Prior Publication Data
US 2020/0129155 A1    Apr. 30, 2020

Related U.S. Application Data

(60) Provisional application No. 62/750,348, filed on Oct. 25, 2018.

(51) Int. Cl.
*A61B 8/00* (2006.01)
*A61B 8/08* (2006.01)

(52) U.S. Cl.
CPC ............ *A61B 8/465* (2013.01); *A61B 8/08* (2013.01); *A61B 8/5207* (2013.01); *A61B 8/5223* (2013.01)

(58) Field of Classification Search
CPC ......... A61B 8/465; A61B 8/08; A61B 8/5207; A61B 8/5223; A61B 8/085; A61B 8/468
See application file for complete search history.

(56) References Cited

U.S. PATENT DOCUMENTS

| | | |
|---|---|---|
| D846,128 S | 4/2019 | de Jonge et al. |
| D846,749 S | 4/2019 | de Jonge et al. |
| D869,663 S | 12/2019 | de Jonge et al. |
| D869,664 S | 12/2019 | de Jonge et al. |
| D869,665 S | 12/2019 | de Jonge et al. |
| D870,295 S | 12/2019 | de Jonge et al. |
| D870,296 S | 12/2019 | de Jonge et al. |
| 2011/0055447 A1 | 3/2011 | Costa |
| 2017/0090675 A1* | 3/2017 | Lee ................. A61B 8/468 |
| 2017/0124700 A1* | 5/2017 | Sarojam ............. A61B 8/46 |

(Continued)

FOREIGN PATENT DOCUMENTS

WO    WO 2017/222970 A1    12/2017

OTHER PUBLICATIONS

International Preliminary Report on Patentability dated May 6, 2021 in connection with International Application No. PCT/US2019/057809.

(Continued)

*Primary Examiner* — Yi-Shan Yang
*Assistant Examiner* — Nicholas A Robinson
(74) *Attorney, Agent, or Firm* — Boston & Galway, LLC

(57) ABSTRACT

Aspects of the technology described herein include a processing device configured to display, on a touch-sensitive display screen of a processing device in operative communication with an ultrasound device, an ultrasound image, a movable measurement tool, and an icon that maintains a fixed distance from a portion of the measurement tool. The icon may be configured to modify the measurement tool, and the icon may not overlap the measurement tool.

13 Claims, 21 Drawing Sheets

(56) References Cited

U.S. PATENT DOCUMENTS

| | | |
|---|---|---|
| 2017/0360397 A1 | 12/2017 | Rothberg et al. |
| 2017/0360399 A1 | 12/2017 | Rothberg et al. |
| 2017/0360401 A1 | 12/2017 | Rothberg et al. |
| 2017/0360402 A1 | 12/2017 | de Jonge et al. |
| 2017/0360403 A1 | 12/2017 | Rothberg et al. |
| 2017/0360404 A1 | 12/2017 | Gafner et al. |
| 2017/0360405 A1 | 12/2017 | Rothberg et al. |
| 2017/0360411 A1 | 12/2017 | Rothberg et al. |
| 2017/0360412 A1 | 12/2017 | Rothberg et al. |
| 2017/0360413 A1 | 12/2017 | Rothberg et al. |
| 2017/0360414 A1 | 12/2017 | Rothberg et al. |
| 2017/0360415 A1 | 12/2017 | Rothberg et al. |
| 2018/0015256 A1* | 1/2018 | Southard .................. G06T 7/62 |
| 2018/0088694 A1 | 3/2018 | Lee et al. |
| 2019/0000418 A1 | 1/2019 | Rothberg et al. |

OTHER PUBLICATIONS

International Search Report and Written Opinion dated Jan. 10, 2020 in connection with International Application No. PCT/US2019/057809.

PCT/US2019/057809, May 6, 2021, International Preliminary Report on Patentability.

PCT/US2019/057809, Jan. 10, 2020, International Search Report and Written Opinion.

\* cited by examiner

METHODS AND APPARATUS FOR PERFORMING MEASUREMENTS ON AN ULTRASOUND IMAGE

CROSS-REFERENCE TO RELATED APPLICATIONS

This application claims the benefit under 35 U.S.C. § 119(e) of U.S. Patent Application Ser. No. 62/750,348, filed Oct. 25, 2018, and entitled "METHODS AND APPARATUS FOR PERFORMING MEASUREMENTS ON AN ULTRASOUND IMAGE", which is hereby incorporated herein by reference in its entirety.

FIELD

Generally, the aspects of the technology described herein relate to ultrasound data collection and analysis.

BACKGROUND

Ultrasound systems may be used to perform diagnostic imaging and/or treatment sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a pulser in an ultrasound imaging device), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound systems, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, a method includes displaying, on a touch-sensitive display screen of a processing device in operative communication with an ultrasound device: an ultrasound image, a movable measurement tool, and an icon that maintains a fixed distance from a portion of the measurement tool, where the icon is configured to modify the measurement tool, and the icon does not overlap the measurement tool.

In some embodiments, the measurement tool comprises a line, the icon maintains the fixed distance from an endpoint of the line, and the icon is configured to control a position of the endpoint of the line. In some embodiments, the measurement tool comprises an ellipse, the icon maintains the fixed distance from a vertex of the ellipse, and the icon is configured to control a length of an axis of the ellipse that includes the vertex. In some embodiments, the measurement tool comprises an ellipse, the icon maintains the fixed distance from a vertex of the ellipse, and the icon is configured to control a rotation of the ellipse.

According to another aspect, a method includes displaying, on a touch-sensitive display screen of a processing device in operative communication with an ultrasound device: an ultrasound image, a line extending between a first endpoint and a second endpoint, and an icon located a fixed distance from the first endpoint along a direction defined by the line; detecting a dragging movement covering a distance in a horizontal direction and/or a distance in a vertical direction across the touch-sensitive display screen, wherein the dragging movement begins on or within a threshold distance of the icon; displaying the first endpoint at a new location on the touch-sensitive display screen that is removed from the endpoint's previous location by the distance in the horizontal direction and/or the distance in the vertical direction; displaying the icon at a new location on the touch-sensitive display screen that is removed from the new location of the first endpoint by the fixed distance along the direction defined by the line; and performing a measurement on the ultrasound image based on the line.

According to another aspect, a method includes displaying, on a touch-sensitive display screen of a processing device in operative communication with an ultrasound device, an ultrasound image and a line extending between a first endpoint and a second endpoint; detecting a dragging movement covering a distance in a horizontal direction and/or a distance in a vertical direction across the touch-sensitive display screen, wherein the dragging movement begins on or within a threshold distance of the line; displaying the first endpoint and the second endpoint of the line at new locations on the touch-sensitive display screen that are removed from their previous locations by the distance in the horizontal direction and/or the distance in the vertical direction; and performing a measurement on the ultrasound image based on the line.

According to another aspect, a method includes displaying, on a touch-sensitive display screen of a processing device in operative communication with an ultrasound device: an ultrasound image; an ellipse having an axis that is either a major axis or a minor axis of the ellipse, wherein the axis extends between a first vertex and a second vertex of the ellipse; and an icon located a fixed distance from the first vertex along a direction defined by the axis; detecting a dragging movement covering a distance along the direction defined by the axis of the ellipse across the touch-sensitive display screen, wherein the dragging movement begins on or within a threshold distance of the icon; displaying the first vertex at a new location on the touch-sensitive display screen that is removed from the first vertex's previous location by the distance along the direction defined by the axis of the ellipse; displaying the second vertex at a new location on the touch-sensitive display screen that is removed from the second vertex's previous location by the distance along the direction defined by the axis of the ellipse; displaying the icon at a new location on the touch-sensitive display screen that is removed from the first vertex's new location by the fixed distance along the direction defined by the axis of the ellipse; and performing a measurement on the ultrasound image based on the ellipse.

According to another aspect, a method includes displaying, on a touch-sensitive display screen of a processing device in operative communication with an ultrasound device: an ultrasound image; an ellipse having an axis that is either a major axis or a minor axis of the ellipse, wherein the axis extends between a first vertex and a second vertex of the ellipse; and an icon located a fixed distance from the first vertex along a direction defined by the axis; detecting a dragging movement covering a distance along and/or a distance orthogonal to the direction defined by the axis of the ellipse across the touch-sensitive display screen, wherein the dragging movement begins on or within a threshold distance of the icon; displaying the first vertex and the second vertex at new locations on the touch-sensitive display screen that are rotated from their previous locations based on the distance that is along and/or the distance orthogonal to the direction defined by the axis of the ellipse; displaying the icon at a new location on the touch-sensitive display screen that is removed from the first vertex's new location by the fixed distance along the direction defined by the axis of the ellipse; and performing a measurement on the ultrasound image based on the ellipse.

According to another aspect, a method includes displaying, on a touch-sensitive display screen of a processing device in operative communication with an ultrasound device: an ultrasound image; an ellipse having an axis that is either a major axis or a minor axis of the ellipse, wherein the axis extends between a first vertex and a second vertex of the ellipse; and an icon located a fixed distance from the first vertex along a direction defined by the axis; detecting a dragging movement covering distance in a horizontal direction and/or a distance in a vertical direction across the touch-sensitive display screen, wherein the dragging movement begins in an interior of the ellipse or within a threshold distance of a boundary of the ellipse; displaying the first vertex and the second vertex at new locations on the touch-sensitive display screen that are removed from their previous locations by the distance in the horizontal direction and/or the distance in the vertical direction; and performing a measurement on the ultrasound image based on the ellipse.

According to another aspect, a method of operating a processing device configured to display ultrasound images includes displaying an ultrasound image on a display screen of the processing device; displaying a measurement tool overlay on the ultrasound image, the measurement tool overlay comprising a target point; displaying, on the display screen, a touch-sensitive measurement tool control icon corresponding to the target point; and in response to receiving touch input to the display screen, moving the target point and the touch-sensitive measurement tool control icon while maintaining a fixed distance between them. In some embodiments, the touch-sensitive measurement tool control icon does not overlap the measurement tool overlay.

Some aspects include at least one non-transitory computer-readable storage medium storing processor-executable instructions that, when executed by at least one processor, cause the at least one processor to perform the above aspects and embodiments. Some aspects include an ultrasound system having a processing device configured to perform the above aspects and embodiments.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
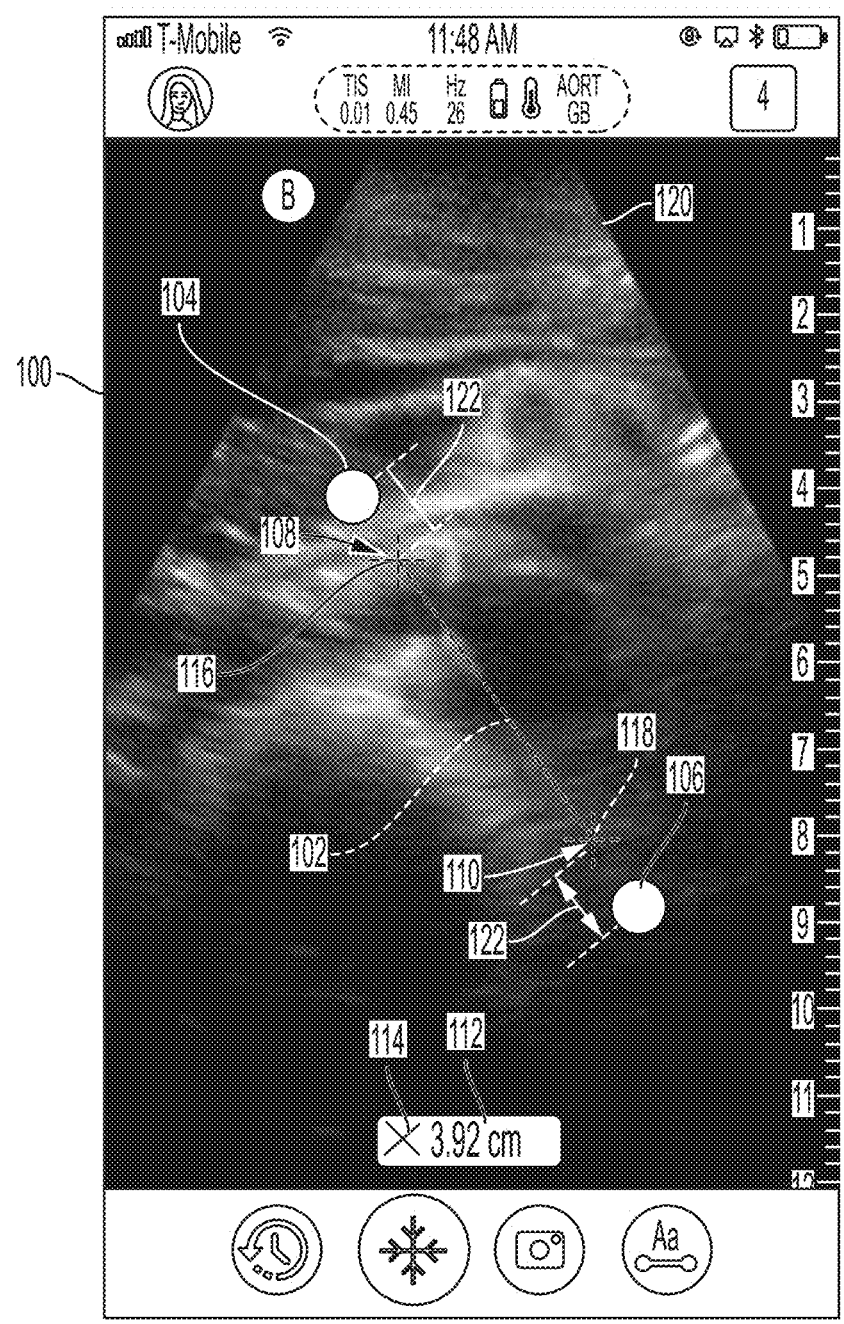
FIG. 1 illustrates an example graphical user interface (GUI) that may be displayed on a touch-sensitive display screen of a processing device in an ultrasound system, in accordance with certain embodiments described herein. The GUI includes a line for performing a measurement on an ultrasound image.

Conventional ultrasound systems are large, complex, and expensive systems that are typically only purchased by large medical facilities with significant financial resources.

Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a-chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application) and published as U.S. Pat. Pub. No. US-2017-0360397-A1, which is incorporated by reference herein in its entirety. Such an ultrasound device may be in operative communication with a processing device, such as a smartphone or a tablet, having a touch-sensitive display screen. The processing device may display ultrasound images generated from ultrasound data collected by the ultrasound device.

The inventors have developed technology for assisting a user in performing measurements on an ultrasound image depicted by the touch-sensitive display screen of a processing device. Performing measurements may include modifying the position, orientation, and/or shape of a measurement tool such as a line or ellipse displayed on the ultrasound image to perform calculations of spatial length or spatial area represented by the ultrasound image. The technology includes icons that are displayed a fixed distance from certain portions of a line or an ellipse, and which in some embodiments do not overlap with any portion of the line or ellipse. The icons may be used to modify the measurement tool. For example, to modify the location of an endpoint of a line, a user may perform a dragging movement across the touch-sensitive display screen that begins on an icon located a fixed distance from the endpoint. The processing device may change the location of the endpoint by a distance corresponding to the distance covered by the dragging movement. The processing device may update, based on the dragging movement, the location of the endpoint at a sufficiently high rate such that the endpoint appears to follow the dragging movement as the dragging movement proceeds. In other words, if a user touches his/her finger to the icon and drags his/her finger across the touch-sensitive display screen, the endpoint may appear to follow the user's finger. Because changing the location of the endpoint may be initiated in this example by the user touching his/her finger to the icon, which may be located a fixed distance away from the endpoint, the endpoint may be removed from the user's finger by the fixed distance as the user drags his/her finger across the touch-sensitive display screen. Thus, as the user drags his/her finger, the endpoint may be visible to the user, and the user may be able to determine when the endpoint has moved to the desired location and release his/her finger from the touch-sensitive display to cause the endpoint to remain in the desired location. Additionally, as described above, in some embodiments the icon may not overlap with any portion of the line, which may further help the user to determine, as s/he drags his/her finger, when the line has been positioned as desired.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

While the description below includes certain methods that a processing device may use to cause a given result to occur, a processing device may implement different methods in order to cause the same result to occur. In particular, code designed to cause the result to occur may implement a different method to cause the result to occur than those described.

FIGS. 1-9 illustrate example graphical user interfaces that may be displayed on a touch-sensitive display screen of a processing device in an ultrasound system, in accordance with certain embodiments described herein. FIGS. 1-5 illustrate examples GUIs that include a line for performing a measurement on an ultrasound image. FIGS. 6-10 illustrate example GUIs that include an ellipse for performing a measurement on an ultrasound image. The processing device may be in operative communication with an ultrasound device. Ultrasound systems and devices are described in more detail with reference to FIGS. 20-21.

FIG. 1 illustrates an example GUI 100 that includes a line 102, a first icon 104, a second icon 106, a first crosshairs 108, a second crosshairs 110, a measurement value indicator 112, a delete option 114, and an ultrasound image 120.

The line 102 extends between a first endpoint 116 and a second endpoint 118. The first crosshairs 108 may help to visually highlight the location of the first endpoint 116 and the second crosshairs 110 may help to visually highlight the location of the second endpoint 118. The line 102 is superimposed on the ultrasound image 120 and may be used to perform a length measurement on the ultrasound image 120. In particular, the processing device may perform a calculation of the spatial length represented by the ultrasound image 120 between the first endpoint 116 and the second endpoint 118. The processing device may receive information from the ultrasound device indicating that the ultrasound image 120 was collected from an area having a certain size. The processing device may use this information to determine the spatial size represented by each pixel and thereby determine the spatial length represented by the line 102. (Similar methods may be used for measurements of spatial length and area using an ellipse, as described below). The spatial length represented by the ultrasound image 120 between the first endpoint 116 and the second endpoint 118 is depicted by the measurement value indicator 112. The user may cause the processing device to modify the locations of the first endpoint 116 and/or the second endpoint 118 on the GUI 100. For example, the user may cause the processing device to modify the locations of the first endpoint 116 and/or the second endpoint 118 to coincide with endpoints of a particular anatomical structure visible in the ultrasound image 120 if the user desires to measure the distance between the endpoints of the anatomical structure. The processing device may update the measurement value indicator 112 based on the new distance between the first endpoint 116 and the second endpoint 118. The processing device may remove the line 102, the first icon 104, and the second icon 106 from the touch-sensitive display in response to a user selection of the delete option 114.

In FIG. 1, the first icon 104 and the second icon 106 are circular, although other forms are possible. Additionally, in FIG. 1, no portion of the first icon 104 or the second icon 106 overlaps the line 102. However, in some embodiments, a portion of the first icon 104 or the second icon 106 may overlap the line 102.

The inventors have developed technology for assisting a user in modifying the locations of the first endpoint 116 and/or the second endpoint 118 (and thereby modifying the position and/or orientation of the line 102) using a touch-sensitive display screen. The technology includes display of the first icon 104 and the second icon 106. The first icon 104 is positioned a fixed distance 122 from the first endpoint 116. The second icon 106 is positioned the fixed distance 122 from the second endpoint 118. In some embodiments, the fixed distance 122 may be a predetermined distance. In some embodiments, the fixed distance 122 may be a default distance. In some embodiments, the fixed distance 122 may be selected by a user. In some embodiments, an icon being positioned a fixed distance from some feature (e.g., an endpoint of the line 102) may mean that the center of the icon is positioned the fixed distance from the feature. In some embodiments, the fixed distance between the first icon 104 and the first endpoint 116 and the fixed distance between the second icon 106 and the second endpoint 118 may not be the same.

The processing device may change the location of the first endpoint 116 based on a dragging movement on the touch-sensitive display screen that begins on or within a threshold distance of the first icon 104. A dragging movement may include, for example, a user touching his/her finger to the touch-sensitive display and dragging his/her finger to a different location on the touch-sensitive display screen. The processing device may change the location of the second endpoint 118 based on a dragging movement on the touch-sensitive display screen that begins on or within a threshold distance of the second icon 106. In particular, if a drag that begins on or within a threshold distance of the first icon 104 covers a certain distance in the horizontal direction and/or a certain distance in the vertical direction, the processing device may change the location of the first endpoint 116 by that same distance in the horizontal direction and/or distance in the vertical direction. (A drag that covers a certain distance in a certain direction need not mean that the drag actually proceeded along that direction, but rather than the drag had a component along that direction. For example, a drag in an arbitrary direction across a touch-sensitive display screen may have a component along the horizontal direction and a component along the vertical direction of the touch-sensitive display screen). If a drag that begins on or within a threshold distance of the second icon 106 covers a certain distance in the horizontal direction and/or a certain distance in the vertical direction, the processing device may change the location of the second endpoint 118 by that same distance in the horizontal direction and/or distance in the vertical direction.

For example, consider the touch-sensitive display screen having an array of pixels, each pixel having a location that is x pixels in the horizontal direction and a location that is y pixels in the vertical location, where x and y are measured from an origin (e.g., a corner of the touch-sensitive display screen). Consider further that the first endpoint is located at e1$x$, e1$y$). When the user performs a dragging movement on the touch-sensitive display screen that begins at a starting location (d1$x$, d1$y$) on or within a threshold distance of the first icon 104 and ends at an ending location (d2$x$, d2$y$), the processing device may change the location of the first endpoint 116 such that the first endpoint 116 is displayed at (e1$x$−(d2$x$−d1$x$), e1$y$+(d2$y$−d1$y$)). The processing device may similarly change the location of the second endpoint 118 based on a drag that begins at or within a threshold distance of the second icon 106. Once the processing device has displayed the first endpoint 116 and/or the second endpoint 118 in a new location, the processing device may display the rest of the line 102 between the first endpoint 116 and/or the second endpoint 118. In some embodiments, the processing device may use the Cartesian equation for a line to determine locations for points along the line that are not endpoints.

The processing device may update, based on a dragging movement, the location of the first endpoint 116 at a sufficiently high rate such that the first endpoint 116 appears to follow the dragging movement as the dragging movement proceeds. In other words, if a user touches his/her finger to the first icon 104 and drags his/her finger across the touch-sensitive display screen, the first endpoint 116 may appear to follow the user's finger. Because changing the location of the first endpoint 116 may be initiated in this example by the user touching his/her finger to the first icon 104, which may be located a fixed distance away from the first endpoint 116, the first endpoint 116 may be removed from the user's finger by the fixed distance as the user drags his/her finger across the touch-sensitive display screen. Thus, as the user drain his/her finger, the first endpoint 116 may be visible to the user, and the user may be able to determine when the first endpoint 116 has moved to the desired location and release his/her finger from the touch-sensitive display to cause the first endpoint 116 to remain in the desired location. The same discussion applies to the second endpoint 118 and the second icon 106.

After a dragging movement that begins at or within a threshold distance of the first icon 104, the processing device may change the location of the first icon 104 such that the first icon 104 is displayed a fixed distance from the first endpoint 116 along a direction defined by the line 102. After a dragging movement that begins at or within a threshold distance of the second icon 106, the processing device may change the location of the second icon 106 such that the second icon 106 is displayed a fixed distance from the second endpoint 118 along a direction defined by the line 102 (i.e., the direction defined by the line 102 after the location of the first endpoint 116 and/or the location of the second endpoint 118 has changed). For example, consider that after the dragging movement, the first endpoint 116 is located at (e1$x$, e1$y$), the second endpoint 118 is located at (e2$x$, e2$y$), and the fixed distance is d. The new location (i1$x$, i1$y$) of the first icon 104 may satisfy the two equations $sqrt((i1x-e1x)^2+(i1y-e1y)^2)=d$ and $(i1y-e1y)/(i1x-e1x)=(e1y-e2y)/(e1x-e2x)$. It should be noted that there may be two sets of solutions for these two equations, and the solution chosen may be the one where (i1$y$, i1$x$) does not coincide with the line 102, meaning that i1$x$ is not between e1$x$ and e2$x$, and i1$y$ is not between e1$y$ and e2$y$. The processing device may similarly change the location of the second icon 106 based on a new position of the second endpoint 118.

In some embodiments, in response to a dragging movement beginning on an icon and covering a distance in the horizontal direction and/or a distance in the vertical direction, the processing device may change the location of the icon by the distance in the horizontal direction and/or the distance in the vertical direction equivalent to the distance in the horizontal direction and/or a distance in the vertical direction covered by the dragging movement, and change the location of the corresponding endpoint to be a fixed distance from the icon's new position along a direction defined by the line. In some embodiments, in response to a dragging movement beginning on an icon and covering a distance in the horizontal direction and/or a distance in the vertical direction, the processing device may change the location of both the endpoint and the icon by the distance in the horizontal direction and/or the distance in the vertical direction equivalent to the distance in the horizontal direction and/or a distance in the vertical direction covered by the dragging movement.

In some embodiments, the processing device may remove the first icon 104 from display during a dragging movement that begins at the first icon 104 and remove the second icon 106 from display during a dragging movement that begins at the second icon 106. This may help the user to understand that the measurement will be performed based on the line 102 and not based on either the first icon 104 or the second icon 106. In other words, this may help the user to understand that the line 102 does not extend to the first icon 104 or the second icon 106. However, in other embodiments, the processing device may continue to display the first icon 104 and the second icon 106 during a dragging movement that begins at the first icon 104 or the second icon 106, respectively.

Figure 2:
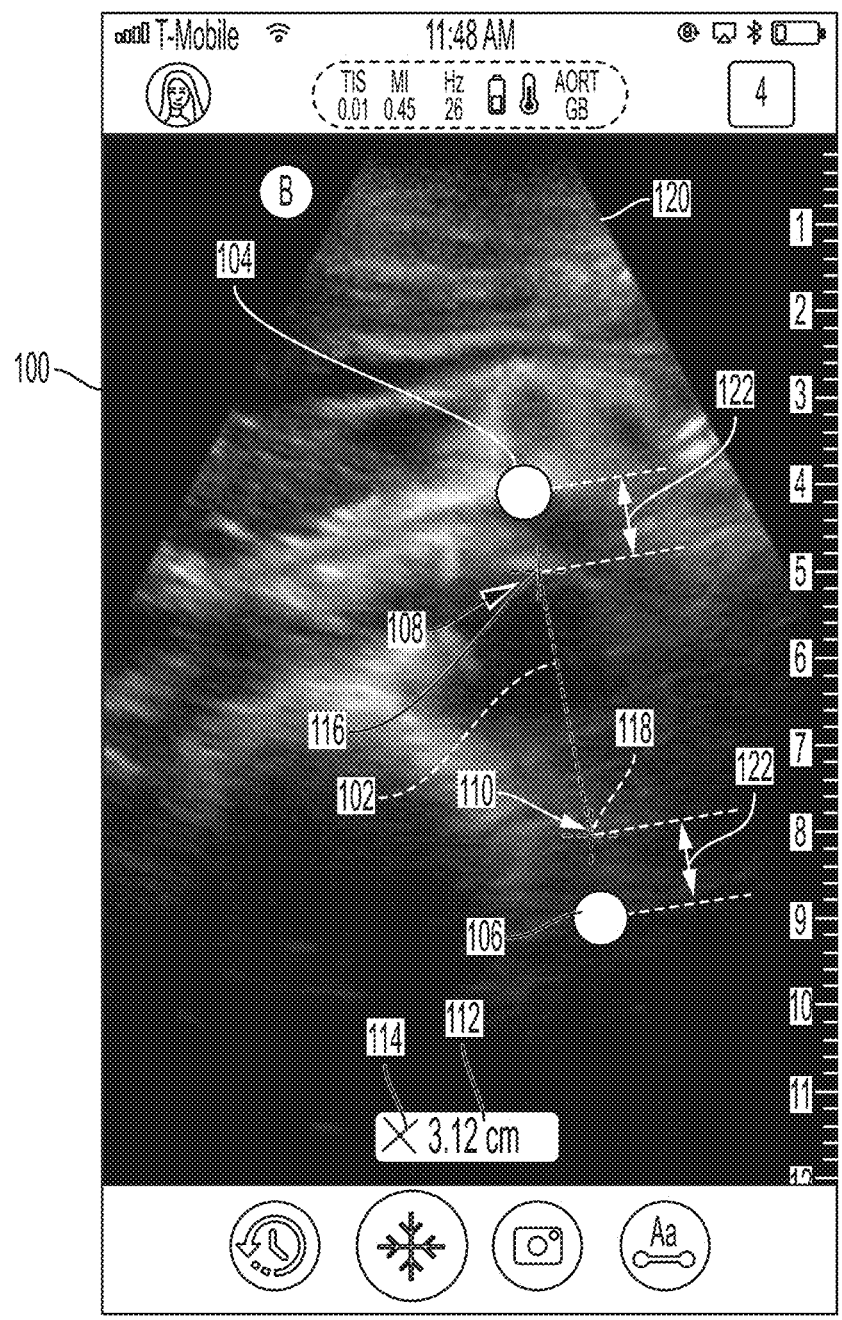
FIG. 2 illustrates another example of the graphical user interface of FIG. 1, in accordance with certain embodiments described herein.

FIG. 2 illustrates the example graphical user interface (GUI) 100 after a dragging movement beginning on or within a threshold distance of the first icon 104. Prior to the dragging movement, the GUI 100 may have appeared as shown in FIG. 1. The processing device has changed the location of the first endpoint 116 from its location in FIG. 1. As described above, the processing device may have changed the location of the first endpoint 116 by a distance in the horizontal direction and/or a distance in the vertical direction equivalent to the distance in the horizontal direction and/or the distance in the vertical direction covered by the dragging movement. The processing device has displayed the rest of the line 102 between the new location of the first endpoint 116 and the previous location of the second endpoint 118. The processing device has also changed the location of the first icon 104 from its location in FIG. 1 to be the fixed distance 122 away from the first endpoint 116 along a direction defined by the line 102. It should be noted that the processing device has changed the measurement value depicted by the measurement value indicator 112 in FIG. 2 from that shown in FIG. 1 based on the change in length of the line 102 from FIG. 1 to FIG. 2.

Figure 3:
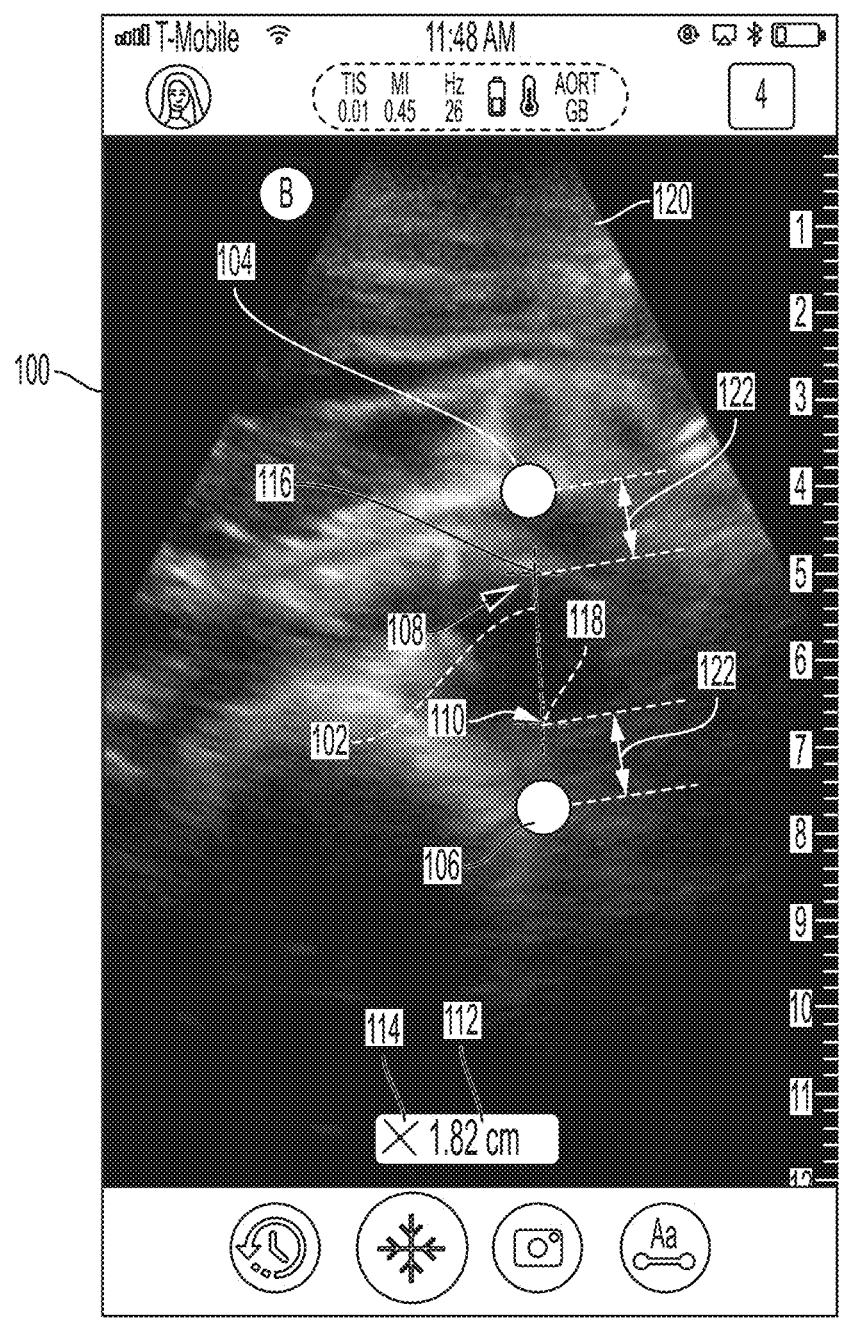
FIG. 3 illustrates another example of the graphical user interface of FIG. 1, in accordance with certain embodiments described herein.

FIG. 3 illustrates the example graphical user interface (GUI) 100 after a dragging movement beginning on or within a threshold distance of the second icon 106. Prior to the dragging movement, the GUI 100 may have appeared as shown in FIG. 2. The processing device has changed the location of the second endpoint 118 from its location in FIG. 1. As described above, the processing device may have changed the location of the second endpoint 118 by a distance in the horizontal direction and/or a distance in the vertical direction equivalent to the distance in the horizontal direction and/or the distance in the vertical direction covered by the dragging movement. The processing device has displayed the rest of the line 102 between the new location of the second endpoint 118 and the previous location of the first endpoint 116. The processing device has also changed the location of the second icon 106 from its location in FIG. 2 to be the fixed distance 122 away from the second endpoint 118 along a direction defined by the line 102. It should be noted that the processing device has changed the measurement value depicted by the measurement value indicator 112 in FIG. 3 from that shown in FIG. 2 based on the change in length of the line 102 from FIG. 2 to FIG. 3.

In some embodiments, the processing device may change the position of both the first endpoint 116 and the second endpoint 118 based on a dragging movement that begins on or within a threshold distance of any portion of the line 102. When the user performs a dragging movement on the touch-sensitive display screen that begins at a starting location (d1x, d1y) on or within a threshold distance of the line 102 and ends at an ending location (d2x, d2y), the processing device may change the locations of both the first endpoint 116 and the second endpoint 118 by a distance of (d2x−d1x, d2y−d1y). The processing device may also change the locations of the first icon 104 and the second icon 106 such that they are the fixed distance 122 away from the first endpoint 116 and the second endpoint 118, respectively, along the direction of the line 102. Once the processing device has displayed the first endpoint 116 and the second endpoint 118 in new locations, the processing device may display the rest of the line 102 between the new locations of the first endpoint 116 and the second endpoint 118. In some embodiments, the processing device may use the Cartesian equation for a line to determine locations for points along the line 102 between the first endpoint 116 and the second endpoint 118. In some embodiments, the processing device may change the locations of all displayed points along the line 102 by a distance of (d2x−d1x, d2y−d1y).

Figure 4:
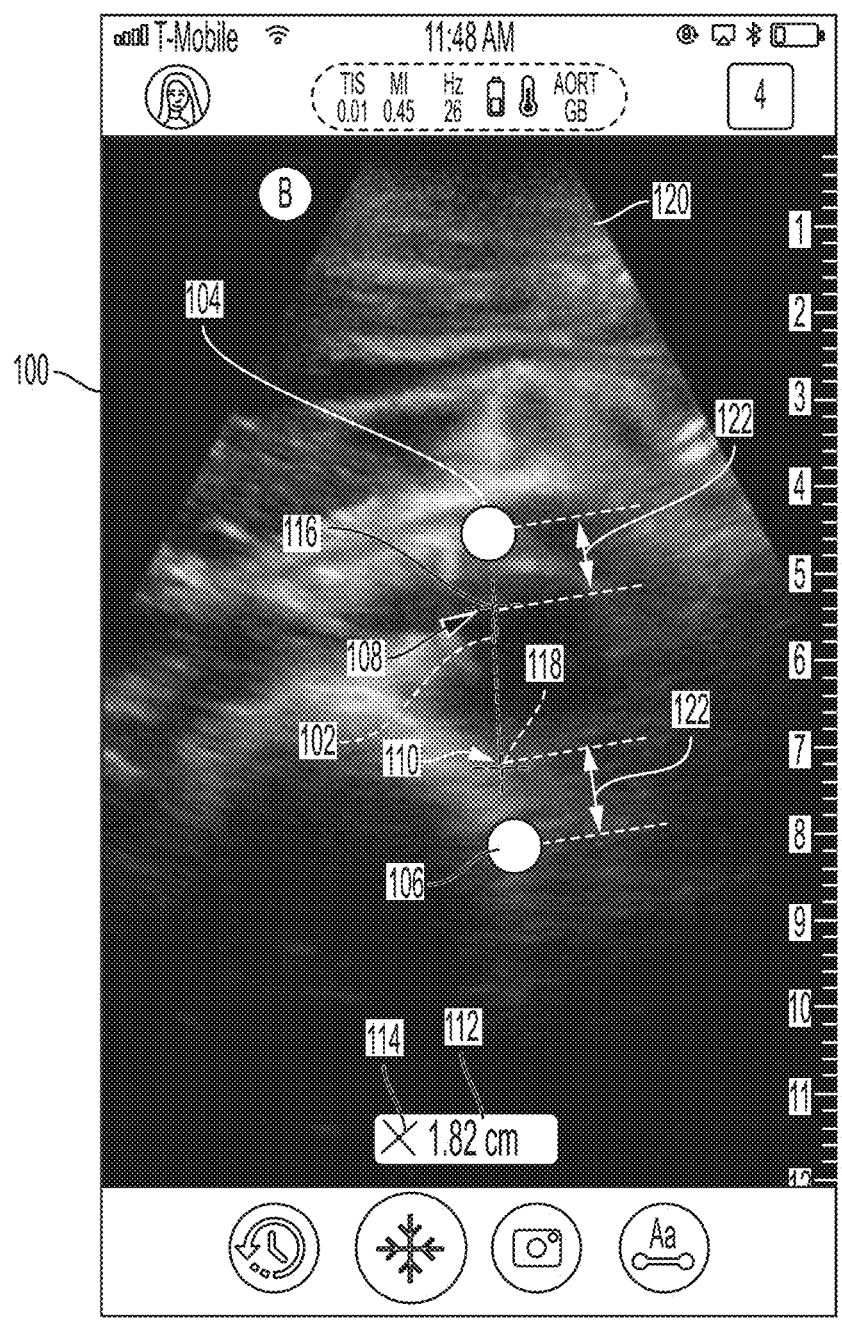
FIG. 4 illustrates another example of the graphical user interface of FIG. 1, in accordance with certain embodiments described herein.

FIG. 4 illustrates the example graphical user interface (GUI) 100 after a dragging movement beginning on or within a threshold distance of the line 102. Prior to the dragging movement, the GUI 100 may have appeared as shown in FIG. 3. The processing device has changed the location of the line from its location in FIG. 3. As described above, the processing device may have changed the location of the first endpoint 116 and the second endpoint 118 by a distance in the horizontal direction and/or a distance in the vertical direction equivalent to the distance in the horizontal direction and/or the distance in the vertical direction covered by the dragging movement. The processing device has displayed the rest of the line 102 between the new locations of the first endpoint 116 and the second endpoint 118. The processing device has also changed the locations of the first icon 104 and the second icon 106 from their locations in FIG. 3 to be the fixed distance 122 away from the first endpoint 116 and the second endpoint 116, respectively, along a direction defined by the line 102.

Figure 5:
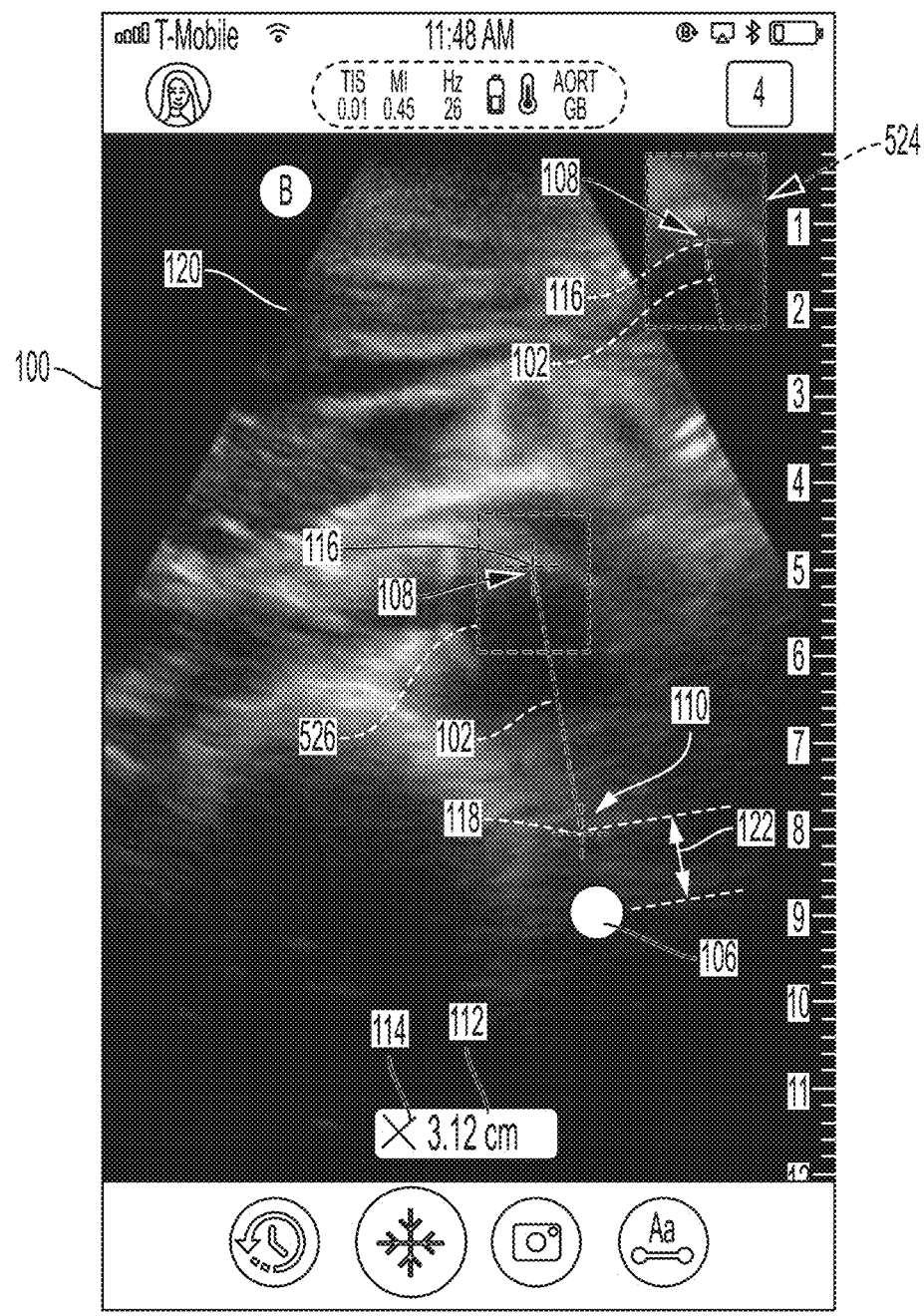
FIG. 5 illustrates another example of the graphical user interface of FIG. 1, in accordance with certain embodiments described herein.

FIG. 5 illustrates the example graphical user interface (GUI) 100 during a dragging movement beginning on or within a threshold distance of the first icon 104. The GUI 100 in FIG. 5 is similar to that shown in FIG. 2, with the addition of an inset 524. The inset 524 depicts a magnification of a portion 526 of the ultrasound image 120. In particular, the inset 524 depicts a portion 526 of the ultrasound image 120 that is proximal to the first endpoint 116. The inset 524 further depicts the first endpoint 116, the first crosshairs 108, and a portion of the line 102 that is within the portion 526 of the ultrasound image 120. The processing device may display the inset 524 when the user begins a dragging movement and continue to display the inset 524 as the user continues the dragging movement. Because the inset 524 illustrates the magnified portion 526 of the ultrasound image 120 that is proximal to the first endpoint 116, the user may use the inset 524 to determine how to perform the dragging movement in order to change the location of the first endpoint 116 to the desired location on the ultrasound image 120, and also to determine when the first endpoint 116 is at the desired location. If the user begins a dragging movement on or within a threshold distance of the second icon 106, the processing device may display the inset 524 and show a magnified portion (not shown in FIG. 5) of the ultrasound image 120 that is proximal to the second endpoint 118, and the inset 524 may also depict the second endpoint 118, the second crosshairs 110, and a portion of the line 102 that is within the portion of the ultrasound image 120 depicted by the inset 524. It should be noted that in FIG. 5, in contrast to FIG. 2, the processing device does not display the first icon 104 during the dragging movement that began on or within a threshold distance of the first icon 104.

However, in some embodiments, the processing may display the first icon 104 during the dragging movement. In some embodiments, the processing device may not display the inset 524 during a dragging movement.

It should be understood that in some embodiments, certain portions of the GUI 100 may be absent. For example, the first crosshairs 108, the second crosshairs 110, and/or the delete option 114 may be absent. In some embodiments, the measurement value indicator 112 may have a different form than shown and/or be located at a different location on the touch-sensitive display screen. Additionally, while the GUI 100 shows certain other features that are not described herein (e.g., certain buttons or indicators), in some embodiments such features may be absent or different.

Figure 6:
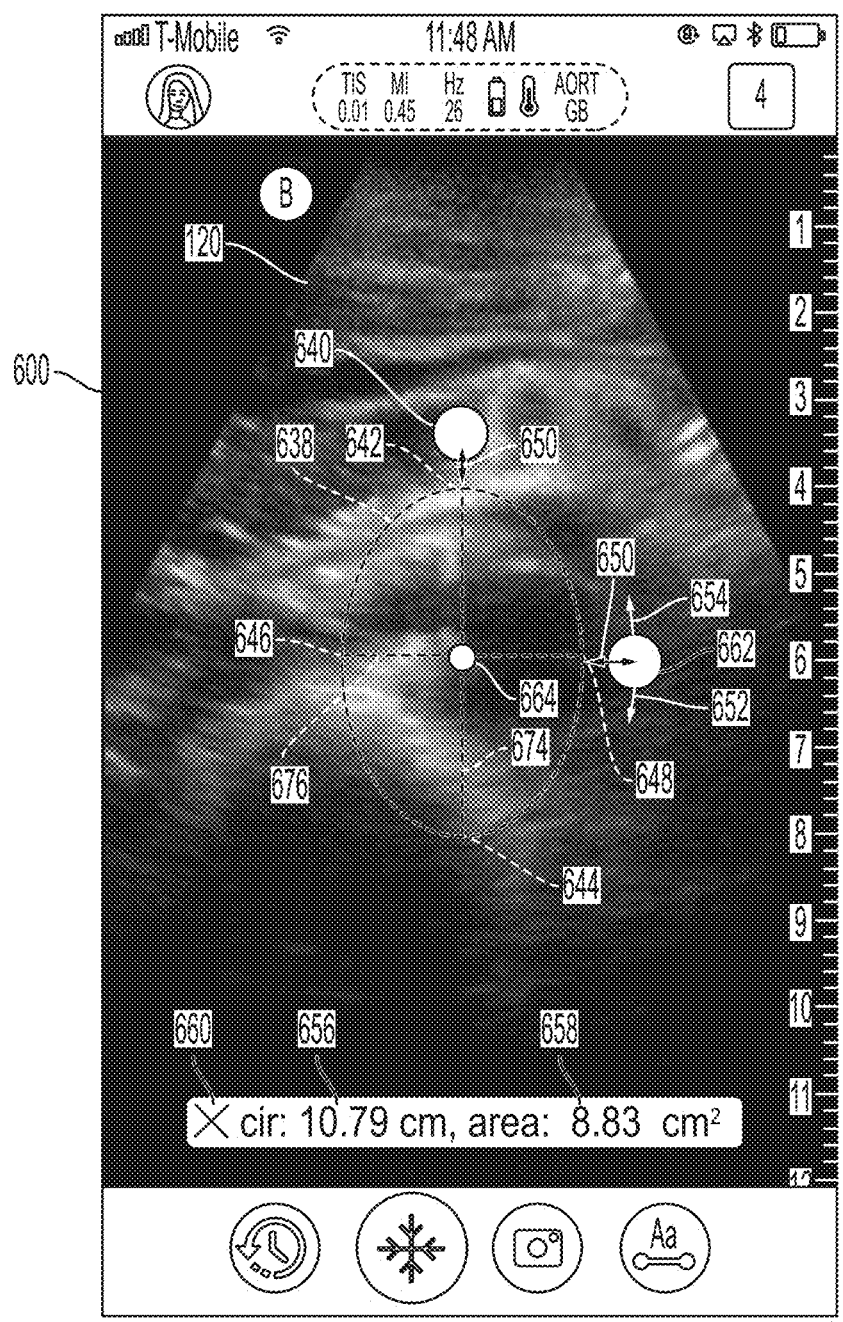
FIG. 6 illustrates an example graphical user interface that may be displayed on a touch-sensitive display screen of a processing device in an ultrasound system, in accordance with certain embodiments described herein. The GUI includes an ellipse for performing a measurement on an ultrasound image.

FIG. 6 illustrates an example graphical user interface (GUI) 600 that includes an ellipse 638, a first icon 640, a second icon 662, a first measurement value indicator 656, a second measurement value indicator 658, a delete option 660, and an ultrasound image 120. The second icon 662 includes a first arrow 652 and a second arrow 654.

The ellipse 638 includes a center location 664, a first axis 674, and a second axis 676. The first axis 674 extends between two endpoints, namely a first vertex 642 and a second vertex 644 of the ellipse 638. The second axis 676 extends between two endpoints, namely a third vertex 646 and a fourth vertex 648 of the ellipse 638. The first axis 674 and the second axis 676 may be equivalent to the major axis and the minor axis of the ellipse, or vice versa. It should be appreciated that the ellipse 638 may be a circle. The ellipse 638 is superimposed on the ultrasound image 120 and may be used by the processing device to perform a measurement on the ultrasound image 120. In FIG. 6, the processing device displays the value of the spatial length represented by the ultrasound image 120 along the circumference of the ellipse 638 with the first measurement value indicator 656 and the processing device displays the value of the spatial area represented by the ultrasound image 120 within the ellipse 638 with the second measurement value indicator 658. The user may cause the processing device to modify the ellipse (e.g., the position, orientation, and/or shape of the ellipse). For example, the user may cause the processing device to modify the ellipse to coincide with a particular anatomical structure visible in the ultrasound image 120 if the user desires to measure the circumference or area of the anatomical structure as depicted by the ultrasound image 120.

The inventors have developed technology for assisting a user in modifying the position, orientation, and shape of the ellipse 638 using a touch-sensitive display screen. The technology includes display of the first icon 640 and the second icon 662. The processing device displays the first icon 640 a fixed distance 650 from the first vertex 642. The processing device displays the second icon 662 the fixed distance 650 from the fourth vertex 648. In some embodiments, the fixed distance 650 may be a predetermined distance. In some embodiments, the fixed distance 650 may be a default distance. In some embodiments, the fixed distance 650 may be selected by a user. In some embodiments, an icon being positioned a fixed distance from some feature (e.g., a vertex of the ellipse 638) may mean that the center of the icon is positioned the fixed distance from the feature. In some embodiments, the fixed distance between the first icon 640 and the first vertex 642 and the fixed distance between the second icon 662 and the third vertex 646 may not be the same.

In FIG. 6, the first icon 640 and the second icon 662 are circular, although other forms are possible. Additionally, in FIG. 6, no portion of the first icon 640 or the second icon 662 overlaps the ellipse 638. However, in some embodiments, a portion of the first icon 640 or the second icon 662 may overlap the ellipse 638.

The processing device may change the length of the first axis 674 based on a dragging movement on the touch-sensitive display screen that begins on or within a threshold distance of the first icon 640. In particular, if the drag that begins on or within a threshold distance of the first icon 640 covers a certain distance away from the ellipse 638 along the direction defined by the first axis 674, the processing device may change the locations of the first vertex 642 and the second vertex 644 by that same distance away from the ellipse along the direction defined by the first axis 674. In other words, the processing device may expand the first axis 674 of the ellipse 638 by two times the distance along the direction defined by the first axis 674. If the drag that begins on or within a threshold distance of the first icon 640 covers a certain distance towards from the ellipse 638 along the direction defined by the first axis 674, the processing device may change the locations of the first vertex 642 and the second vertex 644 by that same distance towards from the ellipse along the direction defined by the first axis 674. In other words, the processing device may contract the first axis 674 of the ellipse 638 by two times the distance along the direction defined by the first axis 674. The processing device may similarly change the length of the second axis 676 based on a dragging movement on the touch-sensitive display screen that begins on or within a threshold distance of the second icon 662. The processing device may display other points along the ellipse 638 based on new lengths of the first axis 674 and/or the second axis 676. For example, the processing device may determine new locations for other points along the ellipse 638 based on the Cartesian equation for an ellipse 638. In some embodiments, to display the ellipse 638 based on the Cartesian equation for an ellipse 638, the processing device may only use the center location 664 of the ellipse, one of the first vertex 642 and the second vertex 644, and one of the third vertex 646 and the fourth vertex 648.

Consider the touch-sensitive display screen having an array of pixels, each pixel having a location that is x pixels in the horizontal direction and a location that is y pixels in the vertical location, where x and y are measured from an origin (e.g., a corner of the touch-sensitive display screen). For simplicity, assume the first axis 674 of the ellipse 638 is parallel to the vertical direction of the touch-sensitive display and the second axis 676 of the ellipse is parallel to the horizontal direction of the touch-sensitive display. Consider further that the first vertex 642 is located at ($v1x$, $v1y$), the second vertex 644 is located at ($v2x$, $v2y$), and the first icon is located at ($i1x$, $i1y$). When the user performs a dragging movement on the touch-sensitive display screen that begins at a starting location ($d1x$, $d1y$) on or within a threshold distance of the first icon 640 and ends at an ending location ($d2x$, $d2y$), the processing device may change the location of the first vertex 642 such that the first vertex 642 is displayed at ($v1x$, $v1y+(d2y-d1y)$). The processing device may also change the location of the second vertex 644 such that the second vertex 644 is displayed at ($v2x$, $v2y-(d2y-d1y)$). As described above, the processing device may display other points along the ellipse 638 based on the new locations of the first vertex 642 and the second vertex 644.

The processing device may update, based on a dragging movement, the location of the first vertex 642 at a sufficiently high rate such that the first vertex 642 appears to follow the dragging movement as the dragging movement proceeds. In other words, if a user touches his/her finger to the first icon 640 and drags his/her finger across the touch-sensitive display screen, the first vertex 642 may appear to follow the user's finger. Because changing the location of the first vertex 642 may be initiated in this example by the user touching his/her finger to the first icon 640, which may be located a fixed distance away from the first vertex 642, the first vertex 642 may be removed from the user's finger by the fixed distance as the user drags his/her finger across the touch-sensitive display screen. Thus, as the user drags his/her finger, the first vertex 642 may be visible to the user, and the user may be able to determine when the first vertex 642 has moved to the desired location and release his/her finger from the touch-sensitive display to cause the first vertex 642 to remain in the desired location. The same discussion applies to the fourth vertex 648 and the second icon 662.

After a dragging movement, the processing device may change the location of the first icon 640 such that the first icon 640 is displayed a fixed distance from the first vertex 642 along the direction defined by the first axis 674. For example, consider that after the dragging movement, the first vertex 642 is located at (v1x, v1y), the second vertex 644 is located at (v2x, v2y), and the fixed distance is d. The new location (i1x, i1y) of the first icon 640 may satisfy the two equations sqrt((i1x−v1x)^2+(i1y−v1y)^2)=d and (i1y−v1y)/(i1x−v1x)=(v1y−v2y)/(v1x−v2x). It should be noted that there may be two sets of solutions for these two equations, and the solution chosen may be the one where (i1y, i1x) is not within the ellipse 630, meaning that i1x is not between v1x and v2x, and i1y is not between v1y and v2y.

In the simplified example described above, the direction defined by the first axis 674 is along the vertical direction of the touch-sensitive display, but in the general case where the direction defined by the first axis 674 is rotated to an angle relative to the vertical direction of the touch-sensitive display, the expressions above may be modified to account for such rotation. In a similar manner as described above regarding changing the location of the first vertex 642, the second vertex 644, and the first icon 640, the processing device may change the location of the third vertex 646, the fourth vertex 648, and the second icon 662 based on a dragging movement that begins on or within a threshold distance of the second icon 662 and covers a certain distance away from/toward the ellipse 638 along the direction defined by the second axis 676.

Figure 7:
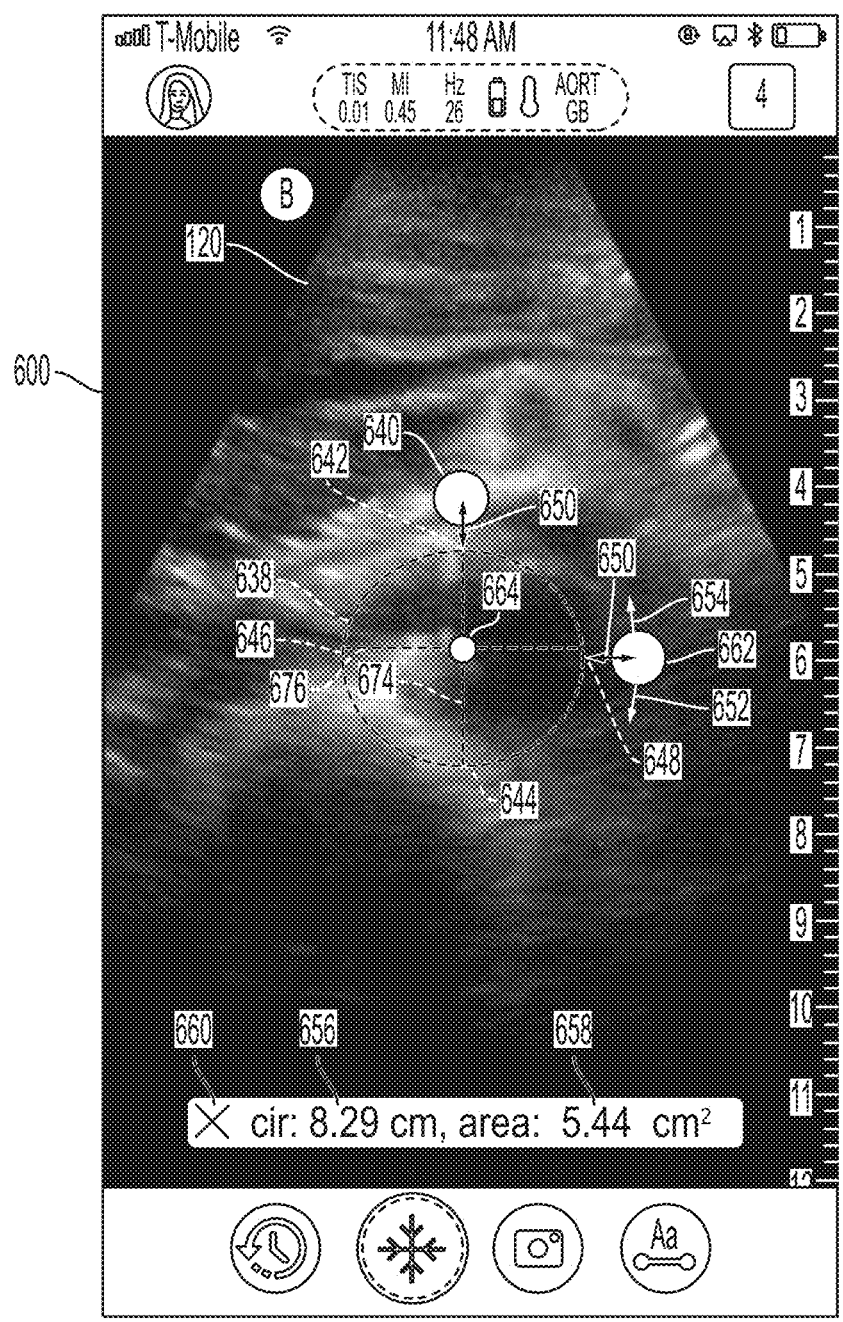
FIG. 7 illustrates another example of the graphical user interface of FIG. 6, in accordance with certain embodiments described herein.

FIG. 7 illustrates the example graphical user interface (GUI) 600 after a dragging movement beginning on or within a threshold distance of the first icon 640 and covering a distance towards the ellipse 638 along the direction of the first axis 674. Prior to the dragging movement, the GUI 600 may have appeared as shown in FIG. 6. The processing device has changed the locations of the first vertex 642 and the second vertex 644 from their locations in FIG. 6. (In other words, the processing device has changed the length of the first axis 674.) As described above, the processing device may have changed the locations of the first vertex 642 and the second vertex 644 by the distance covered by the dragging movement along the direction defined by the first axis 674. The processing device has also changed the location of the first icon 640 from its location in FIG. 6 to be the fixed distance 650 away from the first vertex 674 along a direction defined by the first axis 674. It should be noted that the processing device has changed the measurement values depicted by the first measurement value indicator 656 and the second measurement value indication 658 from that shown in FIG. 6 based on the change in length of the first axis 674 from FIG. 6 to FIG. 7.

Figure 8:
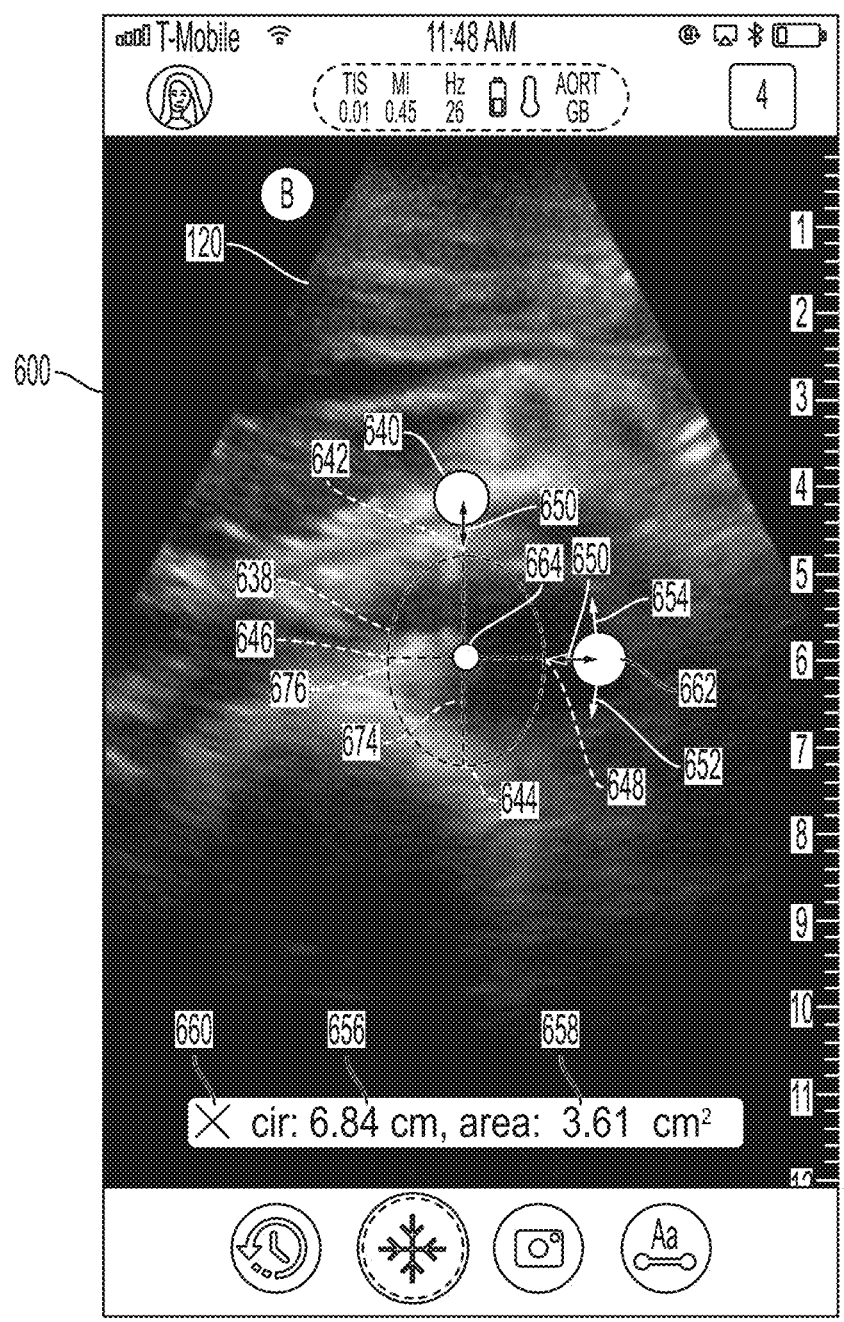
FIG. 8 illustrates another example of the graphical user interface of FIG. 6, in accordance with certain embodiments described herein.

FIG. 8 illustrates the example graphical user interface (GUI) 600 after a dragging movement beginning on or within a threshold distance of the second icon 662 and covering a distance towards the ellipse 638 along the direction of the second axis 676. Prior to the dragging movement, the GUI 600 may have appeared as shown in FIG. 7. The processing device has changed the locations of the third vertex 646 and the fourth vertex 648 from their locations in FIG. 7. (In other words, the processing device has changed the length of the second axis 676.) As described above, the processing device may have changed the locations of the third vertex 646 and the fourth vertex 648 by the distance covered by the dragging movement along the direction defined by the second axis 676. The processing device has also changed the location of the second icon 662 from its location in FIG. 7 to be the fixed distance 650 away from the fourth vertex 648 along a direction defined by the second axis 676. It should be noted that the processing device has changed the measurement values depicted by the first measurement value indicator 656 and the second measurement value indicator 658 from that shown in FIG. 7 based on the change in length of the second axis 676 from FIG. 7 to FIG. 8.

In some embodiments, the processing device may change the position of the ellipse 638 based on a dragging movement that begins in the interior of the ellipse 638, on the boundary of the ellipse 638, or within a threshold distance of the boundary of the ellipse 638. When the user performs a dragging movement on the touch-sensitive display screen that begins at a starting location (d1x, d1y) in the interior of the ellipse 638 or within a threshold distance of the boundary of the ellipse 638 and ends at an ending location (d2x, d2y), the processing device may change the locations of every point on the ellipse 638, as well as the first icon 640 and the second icon 662, by a distance of (d2x−d1x, d2y−d1y). In some embodiments, rather than moving every point on the ellipse 638 by a specific distance, the processing device may change the locations of the center 664 of the ellipse 638, the first vertex 642, the second vertex 644, the third vertex 646, and the fourth vertex 648 by the specific distance and display the rest of the ellipse 638 based on these new locations using the Cartesian equation for an ellipse 638.

Figure 9:
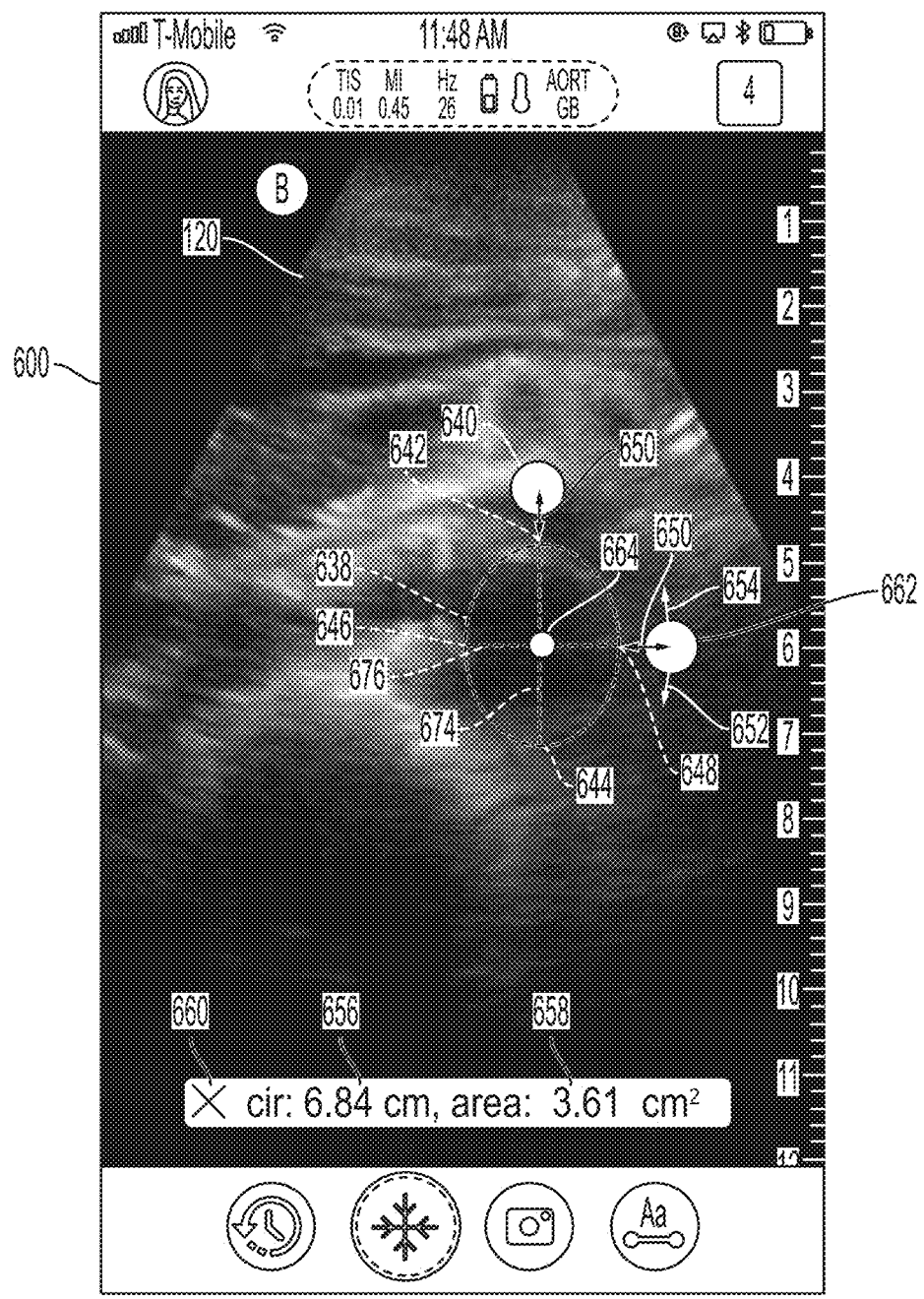
FIG. 9 illustrates another example of the graphical user interface of FIG. 6, in accordance with certain embodiments described herein.

FIG. 9 illustrates the example graphical user interface (GUI) 600 after a dragging movement beginning in the interior of the ellipse 638 or within a threshold distance of the boundary of the ellipse 638. Prior to the dragging movement, the GUI 600 may have appeared as shown in FIG. 8. The processing device has changed the position (but not the orientation or shape) of the ellipse 638 by the distance covered by the dragging movement. The processing device has also changed the location of the first icon 640 from its location in FIG. 8 to be the fixed distance 650 away from the first vertex 674 along a direction defined by the first axis 674, and the location of the second icon 662 from its location in FIG. 8 to be the fixed distance 650 away from the fourth vertex 648 along a direction defined by the second axis 676.

Figure 10:
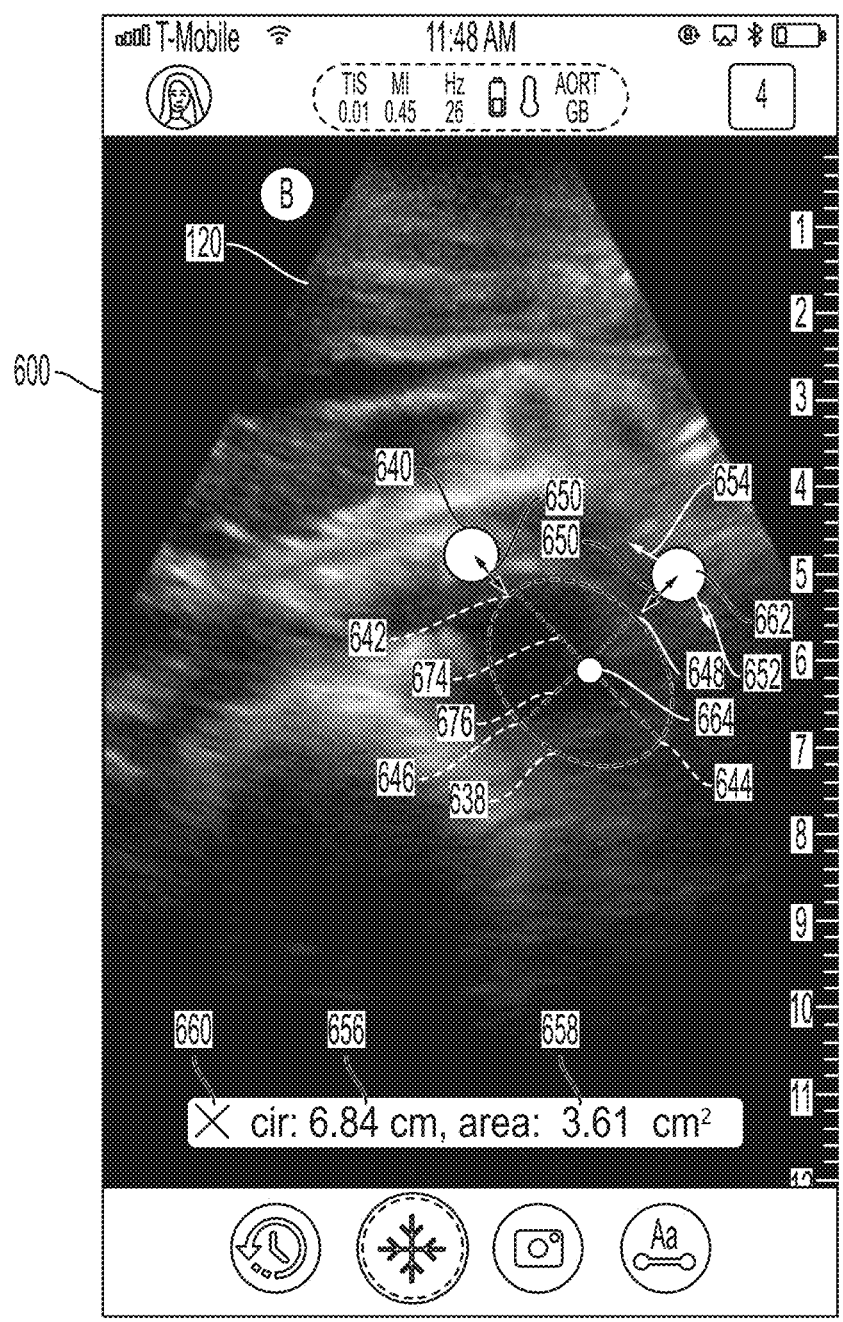
FIG. 10 illustrates another example of the graphical user interface of FIG. 6, in accordance with certain embodiments described herein.

In some embodiments, the processing device may rotate the ellipse 638 based on a dragging movement that begins on or at the second icon 662 and covers a distance along and/or a distance orthogonal to the direction of the second axis 676 of the ellipse 638. FIG. 10 illustrates the example graphical user interface (GUI) 600 after a dragging movement beginning on or within a threshold distance of the second icon 662 and covering a distance along and/or a distance orthogonal to the direction of the second axis 676. Prior to the dragging movement, the GUI 600 may have appeared as shown in FIG. 9. As described above, the processing device has rotated the locations of every point of the ellipse 638 based on the drag distance along and/or the drag distance orthogonal to the direction of the second axis 676. The processing device has also changed the location of the first icon 640 from its location in FIG. 4 to be the fixed distance 650 away from the first vertex 674 along a direction defined by the first axis 674, and the location of the second icon 662 from its location in FIG. 8 to be the fixed distance 650 away from the fourth vertex 648 along a direction defined by the second axis 676.

Figure 11:
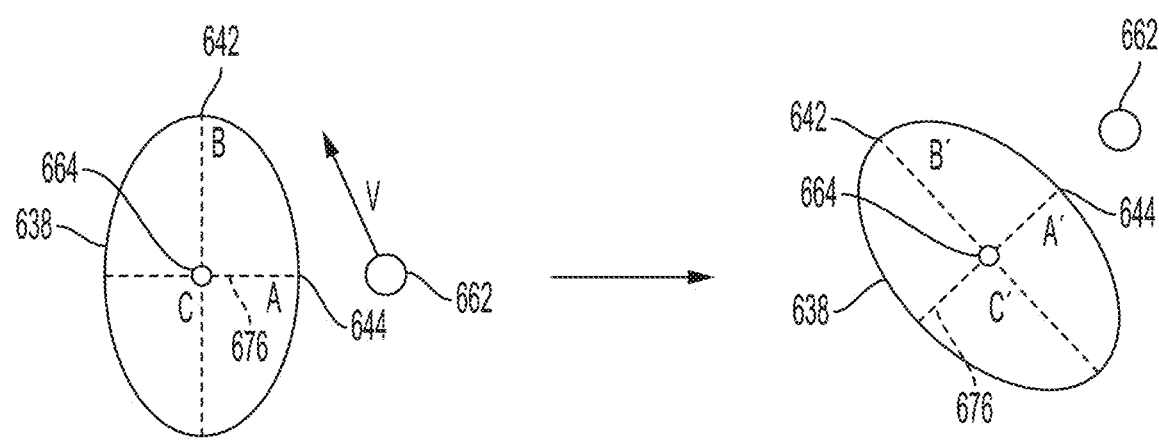
FIG. 11 illustrates a method for determining how much to rotate an ellipse based on a dragging movement, in accordance with certain embodiments described herein.

FIG. 11 illustrates a method for determining how much to rotate the ellipse 638 based on the dragging movement, in accordance with certain embodiments described herein. The left side of FIG. 11 shows the ellipse 638 before the dragging movement and the right side of FIG. 11 shows the ellipse 638 after the dragging movement. For simplicity, before the dragging movement, the center location 664 is labeled C, the second vertex 644 is labeled A, and the first vertex 642 is labeled B. After the dragging movement, the center location 664 is labeled C', the location of the second vertex 644 is labeled A', the location of the first vertex 642 is labeled B', and the location of the second icon 662 is labeled D'. The dragging movement begins at the location of the second icon 662 and ends at a location separated from the previous location by a vector V (where V may have components along and/or orthogonal to the second axis 676). The processing device may determine the location of C' to be the same as C, namely, the center location 664 may not change. The processing device may determine the location of A' to be A+V, in other words, the previous location of the second vertex 644 plus the vector of the dragging movement. The processing device may determine the location of B' to be C+normal($\overline{A'C}$)*length($\overline{BC}$). In other words, the new location of the first vertex 642 may be the center location 664 plus a vector that has a length equal to the distance between the center location 664 and the previous location of the first vertex 642, and a direction that is perpendicular to a vector between the center location 664 and the new location of the second vertex 644. The processing device may determine new locations for the rest of the points on the ellipse 638 based on the new locations for the first vertex 642 and the second vertex 644.

It should be appreciated from the above description of FIG. 11 that rotations of the ellipse 638 may be controlled both by components of a drag distance beginning at or within a threshold distance of the second icon 662 (in other words, the components of the vector V) that are along the direction of the second axis 676 and orthogonal to the direction of the second axis 676. As described above, a dragging movement beginning at or within a threshold distance of the second icon 662 and covering a distance along the direction of the second axis 676 may also control the length of the second axis 676. Thus, a dragging movement beginning at or within a threshold distance of the second icon 662 and having only a component along the direction of the second axis 676 may only modify the length of the second axis 676. A dragging movement beginning at or within a threshold distance of the second icon 662 and having components both along and orthogonal to the direction of the second axis 676 may modify both the length of the second axis 676 and the rotation of the ellipse 638. The description of FIG. 11 may apply both to the general case of a dragging movement having components both along and orthogonal to the direction of the second axis 676, as well as the special case of a dragging movement having a component only along the direction of the second axis 676. In some embodiments, the processing device may use a different method for determining how to rotate an ellipse than the method illustrated by FIG. 11.

The first arrow 652 and the second arrow 654 may serve to indicate to a user that the second icon 662 (as opposed to the first icon 640) can be used to rotate the ellipse 638. In some embodiments, the positioning of the first arrow 652 and the second arrow 654 may change as the shape of the ellipse 638 changes so that the arrows approximate the curvature of the ellipse 638.

It should be understood that in some embodiments, certain portions of the GUI 600 may be absent. For example, the second arrow 654, the first arrow 652, the first measurement value indicator 656, the second measurement value indicator 658, and/or the delete option 660 may be absent. In some embodiments, the first measurement value indicator 656 and/or the second measurement value indicator 658 may have different forms than shown and/or be located at a different locations on the touch-sensitive display screen. Additionally, while the GUI 600 shows certain other features that are not described herein (e.g., certain buttons or indicators), in some embodiments such features may be absent or different.

While the above description has described that a processing device may perform certain calculations using pixels, in some embodiments the processing device may perform calculations using points. It should be noted that certain calculations described herein may produce fractional pixel results. In some embodiments, fractional pixel results may be rounded to a whole pixel. In some embodiments, the processing device may use antialiasing to interpret pixel values for a fractional pixel result (e.g., to interpret pixel values for pixels (1, 1) and (2, 1) when a calculation indicates that something should be displayed at pixel (1.5, 1)). As described above, the processing device may change the location of one feature of a measurement tool (e.g., a line or an ellipse) based on a dragging movement that begins on or within a threshold distance of a certain feature. In some embodiments, the distance may be measured in pixels (e.g., 30 pixels). While the above description has described a touch-sensitive display screen, in some embodiments the screen may not be touch-sensitive display screen, and a click and drag of a cursor (e.g., using a mouse) may be the equivalent of a dragging movement.

Figure 12:
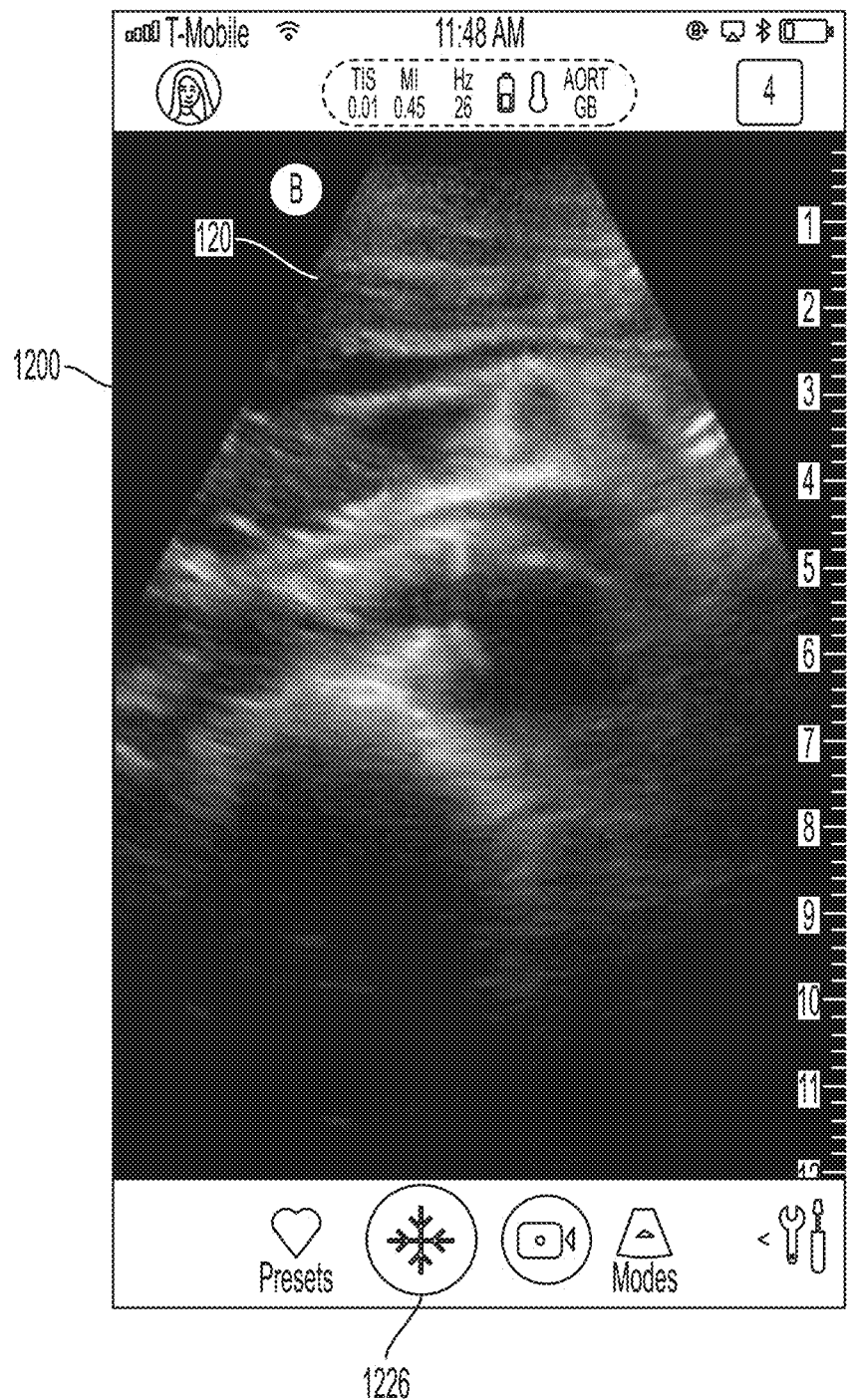
FIG. 12 illustrates an example GUI that may be shown when ultrasound data is being collected, in accordance with certain embodiments described herein.

FIG. 12 illustrates an example GUI 1200 that may be shown when ultrasound data is being collected, in accordance with certain embodiments described herein. The GUI 1200 depicts the most recent ultrasound image 120 collected by the processing device from the ultrasound device. As further ultrasound images 120 are collected, the processing device may continuously update the GUI 1200 to depict the most recent ultrasound image 120 collected. The GUI 1200 further includes a freeze option 1226.

Figure 13:
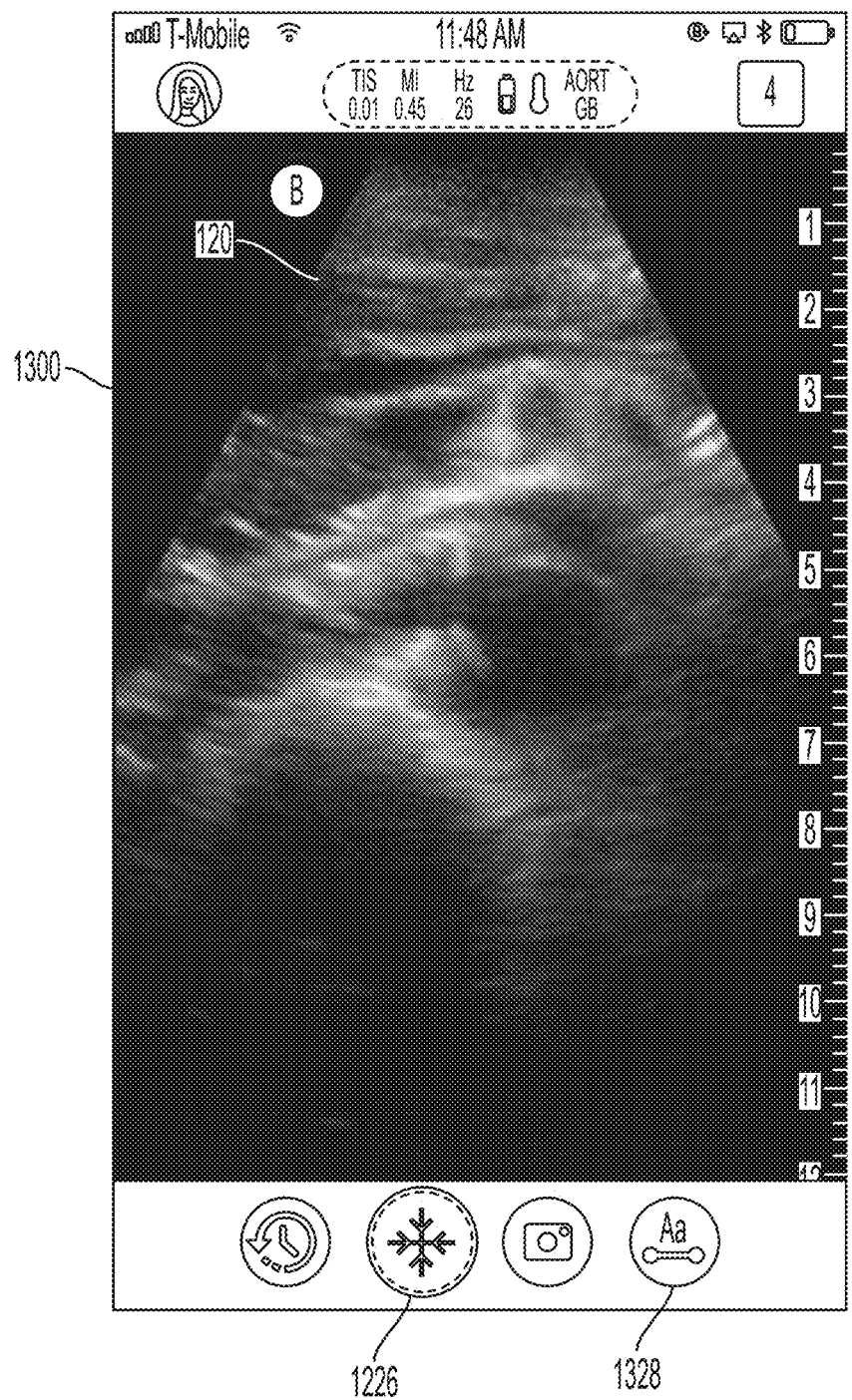
FIG. 13 illustrates an example GUI that may be shown upon selection of a freeze option from the GUI of FIG. 12, in accordance with certain embodiments described herein.

FIG. 13 illustrates an example GUI 1300 that may be shown upon selection of the freeze option 1226, in accordance with certain embodiments described herein. The GUI 1300 depicts the most recent ultrasound image 120 collected by the processing device from the ultrasound device when the freeze option 1226 was selected. In other words, the processing device freezes the most recent ultrasound 120 on the GUI 1300, and the processing device may not update the GUI 1300 with ultrasound images 120 that are collected subsequently. In the GUI 1300, the freeze option 1226 can have a different color or pattern, which may indicate that the GUI 1300 is currently showing a frozen ultrasound image 120. Additionally, the GUI 1300 depicts a measurement option 1328.

Figure 14:
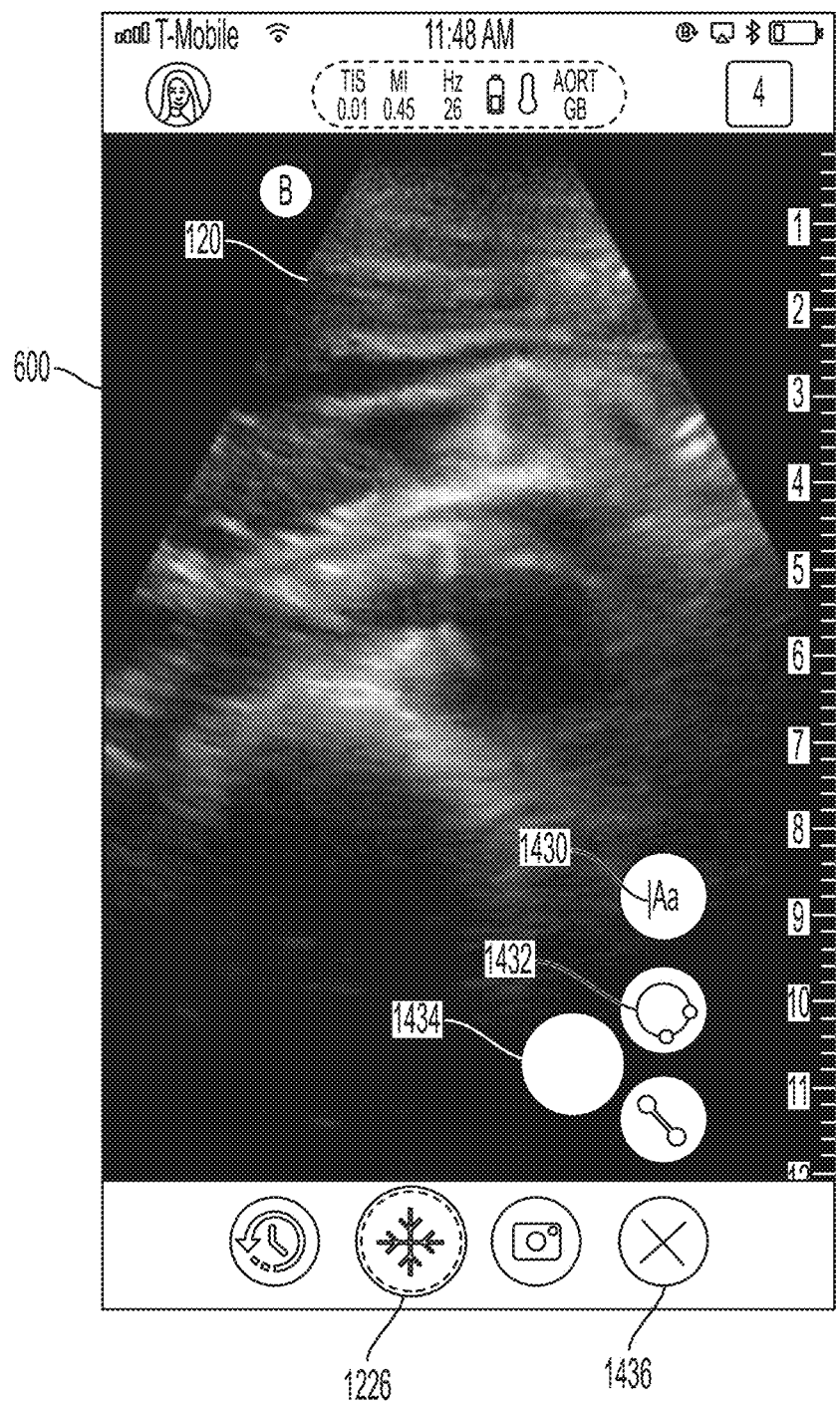
FIG. 14 illustrates an example GUI that may be shown upon selection of a measurement option from FIG. 1:3, in accordance with certain embodiments described herein.

FIG. 14 illustrates an example GUI 1400 that may be shown upon selection of the measurement option 1328, in accordance with certain embodiments described herein. The GUI 1400 can depict the freeze option 1226 having a different color or pattern as explained with respect to FIG. 13, as well as a label option 1430, an ellipse measurement option 1432, a line measurement option 1434, and a menu close option 1436. Upon selection of the label option 1430, the processing device may display a GUI enabling a user to place labels on the ultrasound image 130. Upon selection of the ellipse measurement option 1432, the processing device may display the GUI 600, with the ellipse 638, the first icon 640, and the second icon 662 shown in default positions. Upon selection of the line measurement option 1434, the processing device may display the GUI 100, with the line 102, the first icon 104, and the second icon 106 shown in default positions. Upon selection of the menu close option 1436, the processing device may display the GUI 1300 (i.e., remove from display the label option 1430, the ellipse measurement option 1432, and the line measurement option 1434).

FIGS. 15-19 illustrate example processes for performing measurements on an ultrasound image, in accordance with certain embodiments described herein. The processes may be performed by a processing device in an ultrasound system. The processing device may be, for example, a mobile phone, tablet, or laptop in operative communication with an ultrasound probe. The ultrasound probe and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

Figure 15:
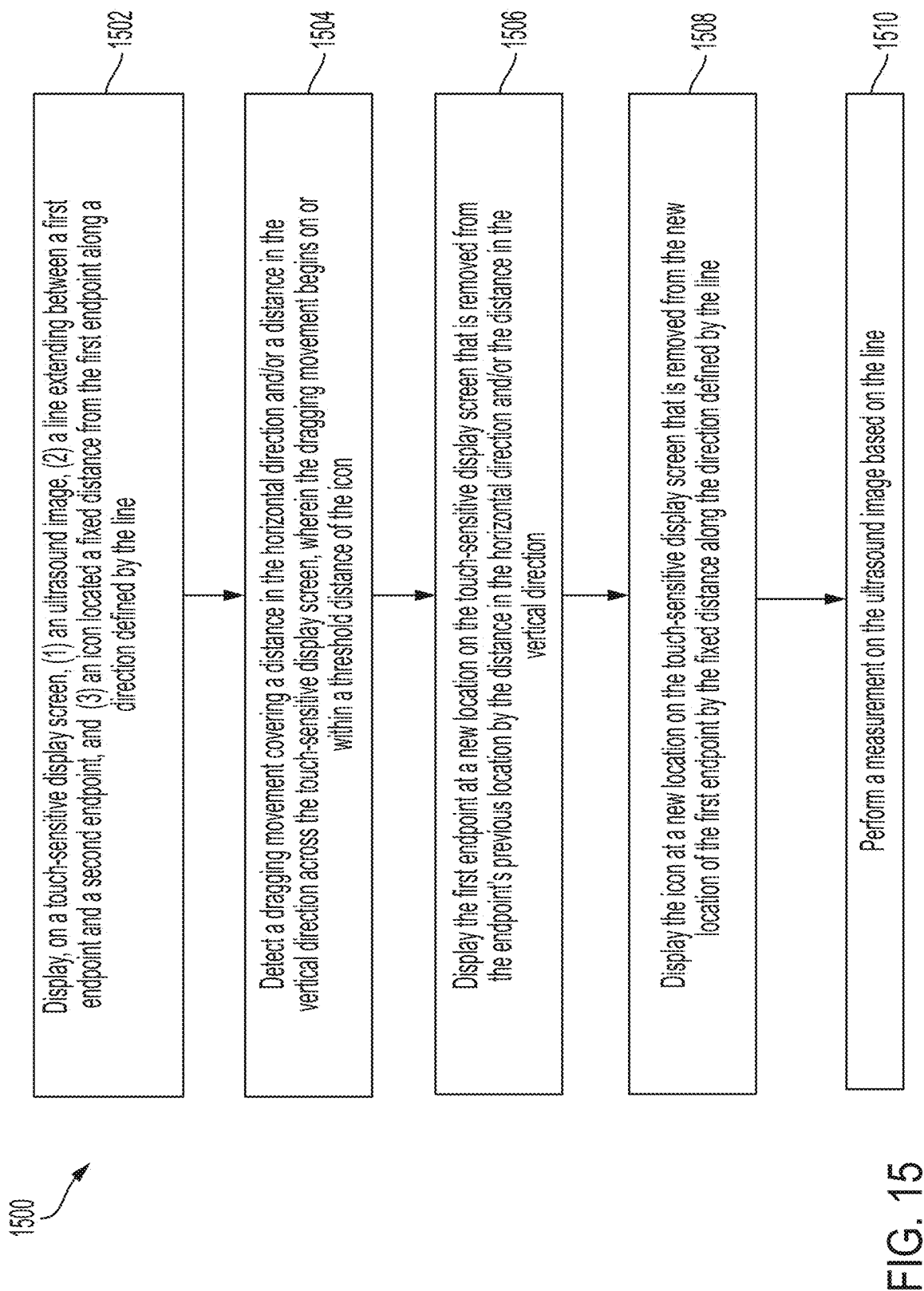
FIG. 15 illustrates an example process for performing measurements on an ultrasound image based on a line, in accordance with certain embodiments described herein.

FIG. 15 illustrates an example process 1500 for performing measurements on an ultrasound image based on a line, in accordance with certain embodiments described herein. Further description of the process 1500 may be found with reference to FIGS. 1-5.

In act 1502, the processing device displays, on a touch-sensitive display screen, (1) an ultrasound image, (2) a line extending between a first endpoint and a second endpoint and (3) an icon located a fixed distance from the first endpoint along a direction defined by the line. The process 1500 proceeds from act 1502 to act 1504.

In act 1504, the processing device detects a dragging movement covering a distance in the horizontal direction and/or a distance in the vertical direction across the touch-sensitive display screen, where the dragging movement begins on or within a threshold distance of the icon. The process 1500 proceeds from act 1504 to act 1506.

In act 1506, the processing device displays the first endpoint at a new location on the touch-sensitive display screen that is removed from the endpoint's previous location by the distance in the horizontal direction and/or the distance in the vertical direction covered by the dragging movement. The process 1500 proceeds from act 1506 to act 1508.

In act 1508, the processing device displays the icon at a new location on the touch-sensitive display screen that is removed from the new location of the first endpoint by the fixed distance along the direction defined by the line. The process 1500 proceeds from act 1508 to act 1510.

In act 1510, the processing device performs a measurement on the ultrasound image based on the line. For example, the processing device may perform a calculation of the spatial length represented by the ultrasound image between the first endpoint and the second endpoint of the line. In some embodiments, the processing device may display the result of the measurement.

In some embodiments, certain acts of the process 1500 may be absent. For example, in some embodiments, act 1510 may be absent. In some embodiments, acts 1504-1510 may be absent. In some embodiments, acts 1504-1508 may be absent. In some embodiments, other combinations of acts may be absent.

Figure 16:
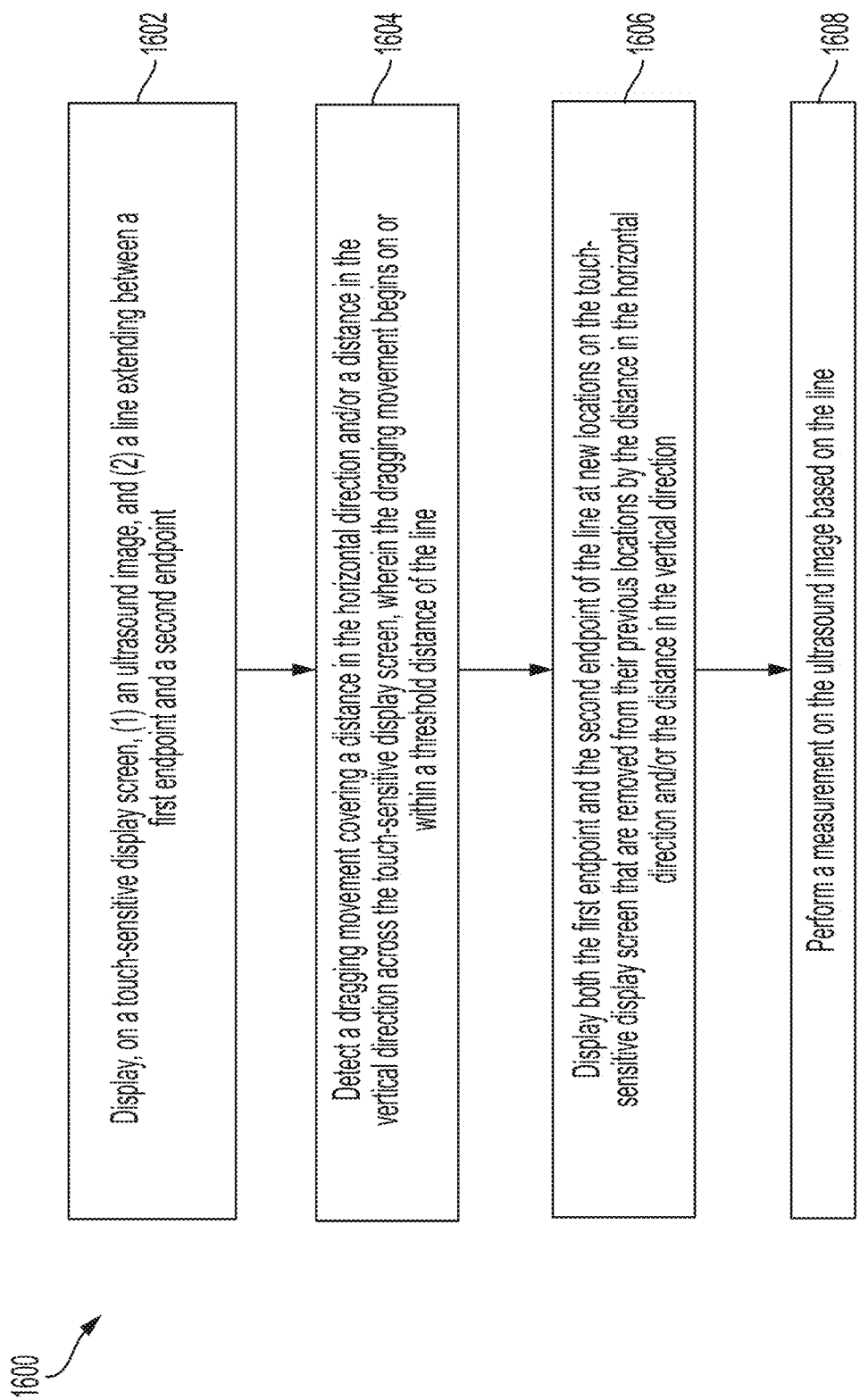
FIG. 16 illustrates an example process for performing measurements on an ultrasound image based on a line, in accordance with certain embodiments described herein.

FIG. 16 illustrates an example process 1600 for performing measurements on an ultrasound image based on a line, in accordance with certain embodiments described herein. Further description of the process 1600 may be found with reference to FIG. 4.

In act 1602, the processing device displays, on a touch-sensitive display screen, (1) an ultrasound image and (2) a line extending between a first endpoint and a second endpoint. The process 1600 proceeds from act 1602 to act 1604.

In act 1604, the processing device detects a dragging movement covering a distance in the horizontal direction and/or a distance in the vertical direction across the touch-sensitive display screen, where the dragging movement begins on or within a threshold distance of the line. The process 1600 proceeds from act 1604 to act 1606.

In act 1606, the processing device displays both the first endpoint and the second endpoint of the line at new locations on the touch-sensitive display screen that are removed from their previous locations by the distance in the horizontal direction and/or the distance in the vertical direction. The process 1600 proceeds from act 1606 to act 1608.

In act 1608, the processing device performs a measurement on the ultrasound image based on the line. For example, the processing device may perform a calculation of the spatial length represented by the ultrasound image between the first endpoint and the second endpoint of the line. In some embodiments, the processing device may display the result of the measurement.

In some embodiments, certain acts of the process 1600 may be absent. For example, in some embodiments, act 1608 may be absent. In some embodiments, acts 1604-1608 may be absent. In some embodiments, acts 1604-1606 may be absent. In some embodiments, other combinations of acts may be absent.

Figure 17:
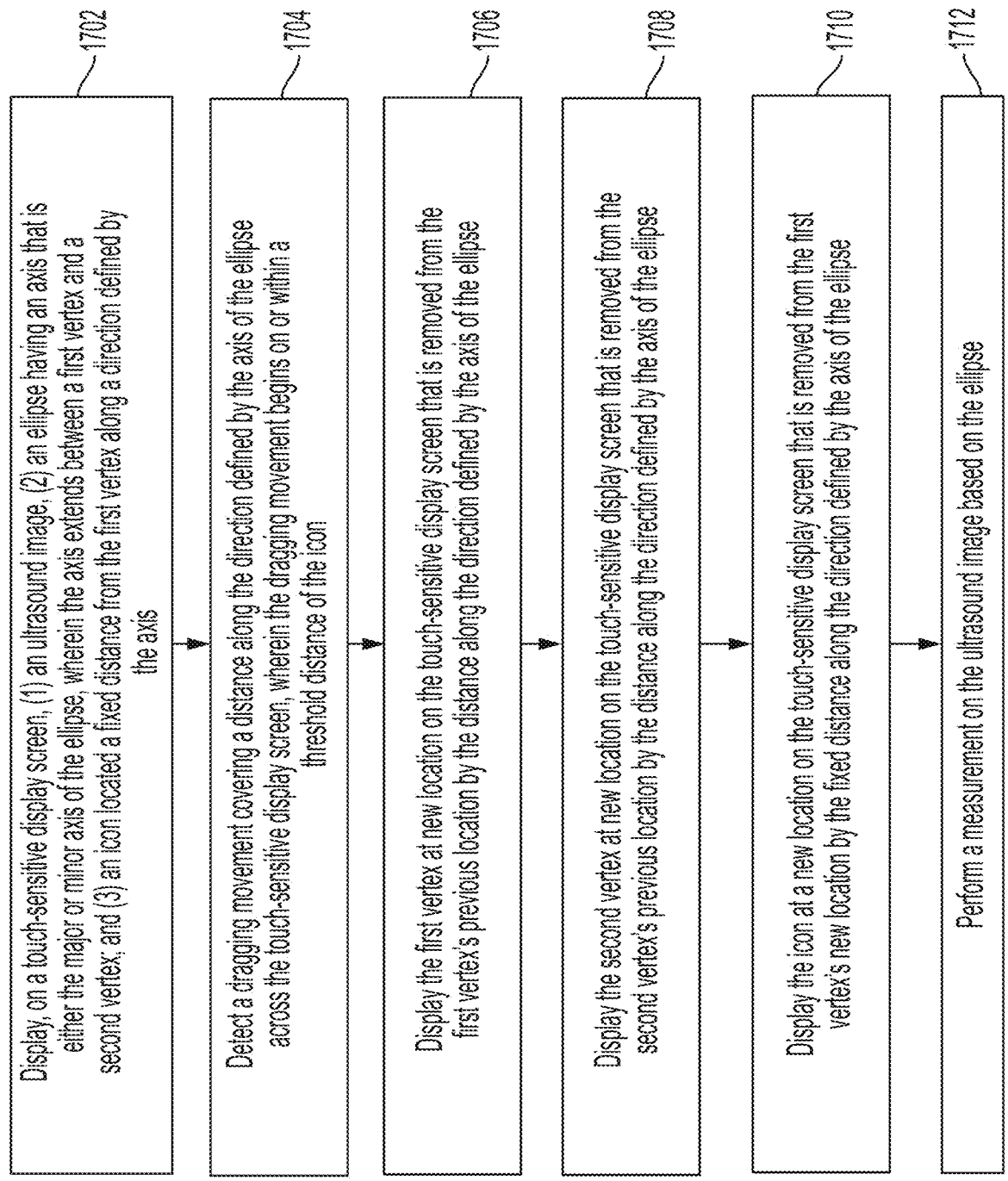
FIG. 17 illustrates an example process for performing measurements on an ultrasound image based on a line, in accordance with certain embodiments described herein.

FIG. 17 illustrates an example process 1700 for performing measurements on an ultrasound image based on an ellipse, in accordance with certain embodiments described herein. Further description of the process 1700 may be found with reference to FIGS. 6-8.

In act 1702, the processing device displays, on a touch-sensitive display screen, (1) an ultrasound image, (2) an ellipse having an axis that is either the major or minor axis of the ellipse, where the axis extends between a first vertex and a second vertex; and (3) an icon located a fixed distance from the first vertex along a direction defined by the axis. The process 1700 proceeds from act 1702 to act 1704.

In act 1704, the processing device detects a dragging movement covering a distance along the direction defined by the axis of the ellipse across the touch-sensitive display screen, where the dragging movement begins on or within a threshold distance of the icon. The process 1700 proceeds from act 1704 to act 1706.

In act 1706, the processing device displays the first vertex at a new location on the touch-sensitive display screen that is removed from the first vertex's previous location by the distance along the direction defined by the axis of the ellipse covered by the dragging movement. The process 1700 proceeds from act 1706 to act 1708.

In act 1708, the processing device displays the second vertex at a new location on the touch-sensitive display screen that is removed from the second vertex's previous location by the distance along the direction defined by the axis of the ellipse covered by the dragging movement. The process 1700 proceeds from act 1708 to act 1710.

In act 1710, the processing device displays the icon at a new location on the touch-sensitive display screen that is removed from the first vertex's new location by the fixed distance along the direction defined by the axis of the ellipse. The process 1700 proceeds from act 1710 to act 1712.

In act 1712, the processing device performs a measurement on the ultrasound image based on the ellipse. For example, the processing device may perform a calculation of the spatial length represented by the ultrasound image along the circumference of the ellipse or a calculation of the spatial area represented by the ultrasound image within the ellipse. In some embodiments, the processing device may display the result of the measurement.

In some embodiments, certain acts of the process 1700 may be absent. For example, in some embodiments, act 1712 may be absent. In some embodiments, acts 1704-1712 may be absent. In some embodiments, acts 1704-1710 may be absent. In some embodiments, other combinations of acts may be absent.

Figure 18:
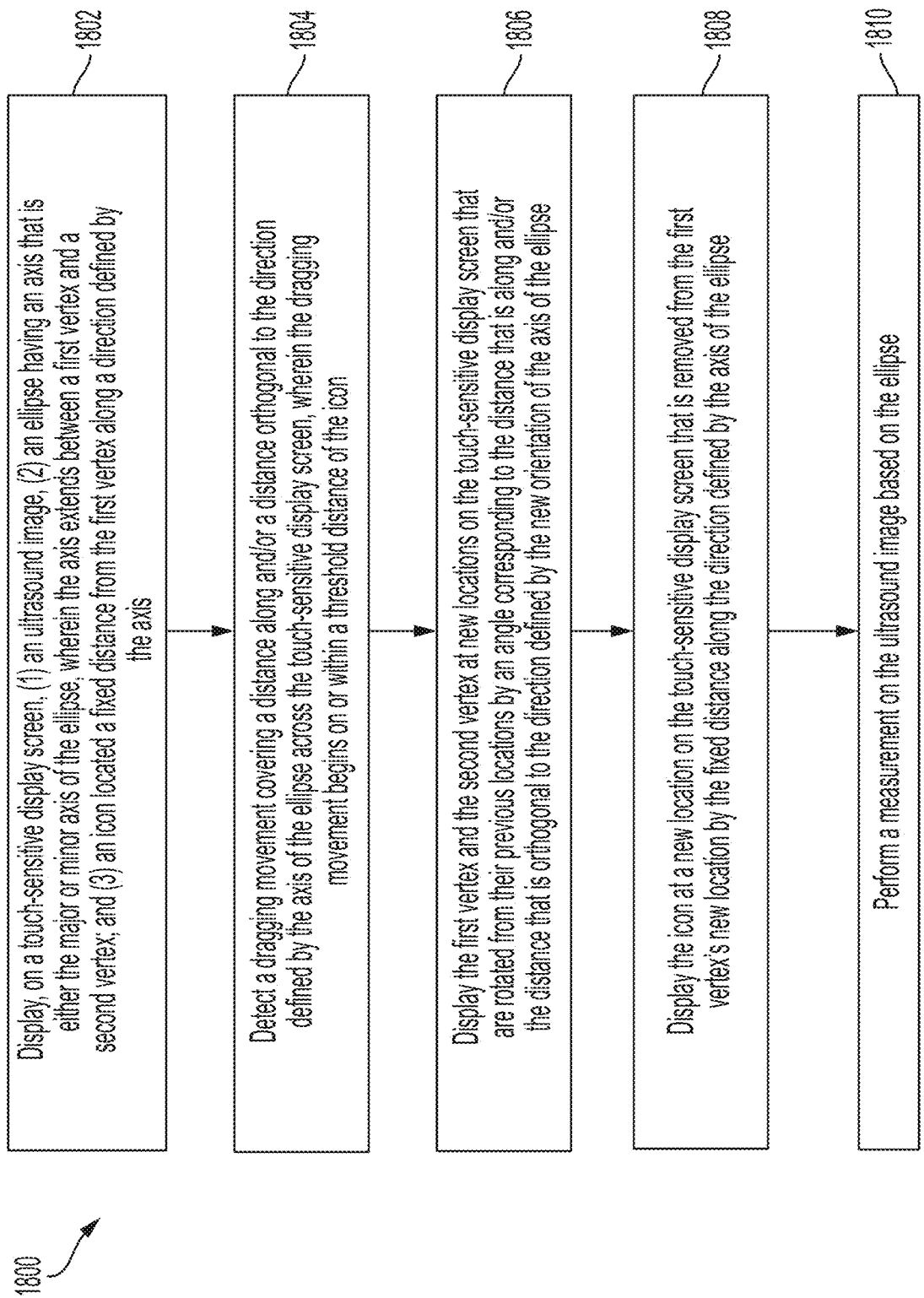
FIG. 18 illustrates an example process for performing measurements on an ultrasound image based on a line, in accordance with certain embodiments described herein.

FIG. 18 illustrates an example process 1800 for performing measurements on an ultrasound image based on an ellipse, in accordance with certain embodiments described herein. Further description of the process 1800 may be found with reference to FIGS. 10-11.

In act 1802, the processing device displays, on a touch-sensitive display screen, (1) an ultrasound image, (2) an ellipse having an axis that is either the major or minor axis of the ellipse, where the axis extends between a first vertex and a second vertex; and (3) an icon located a fixed distance from the first vertex along a direction defined by the axis. The process 1800 proceeds from act 1802 to act 1804.

In act 1804, the processing device detects a dragging movement covering a distance along and/or a distance orthogonal to the direction defined by the axis of the ellipse across the touch-sensitive display screen, where the dragging movement begins on or within a threshold distance of the icon. The process 1800 proceeds from act 1804 to act 1806.

In act 1806, the processing device displays the first vertex and the second vertex at new locations on the touch-sensitive display screen that are rotated from their previous locations based on the distance along and/or the distance orthogonal to the direction defined by the axis of the ellipse that is covered by the dragging movement. The process 1800 proceeds from act 1806 to act 1808.

In act 1808, the processing device displays the icon at a new location on the touch-sensitive display screen that is removed from the first vertex's new location by the fixed distance along the direction defined by the axis of the ellipse. The process 1800 proceeds from act 1808 to act 1810.

In act 1810, the processing device performs a measurement on the ultrasound image based on the ellipse. For example, the processing device may perform a calculation of the spatial length represented by the ultrasound image along the circumference of the ellipse or a calculation of the spatial area represented by the ultrasound image within the ellipse. In some embodiments, the processing device may display the result of the measurement.

In some embodiments, certain acts of the process 1800 may be absent. For example, in some embodiments, act 1810 may be absent. In some embodiments, acts 1804-1810 may be absent. In some embodiments, acts 1804-1808 may be absent. In some embodiments, other combinations of acts may be absent.

Figure 19:
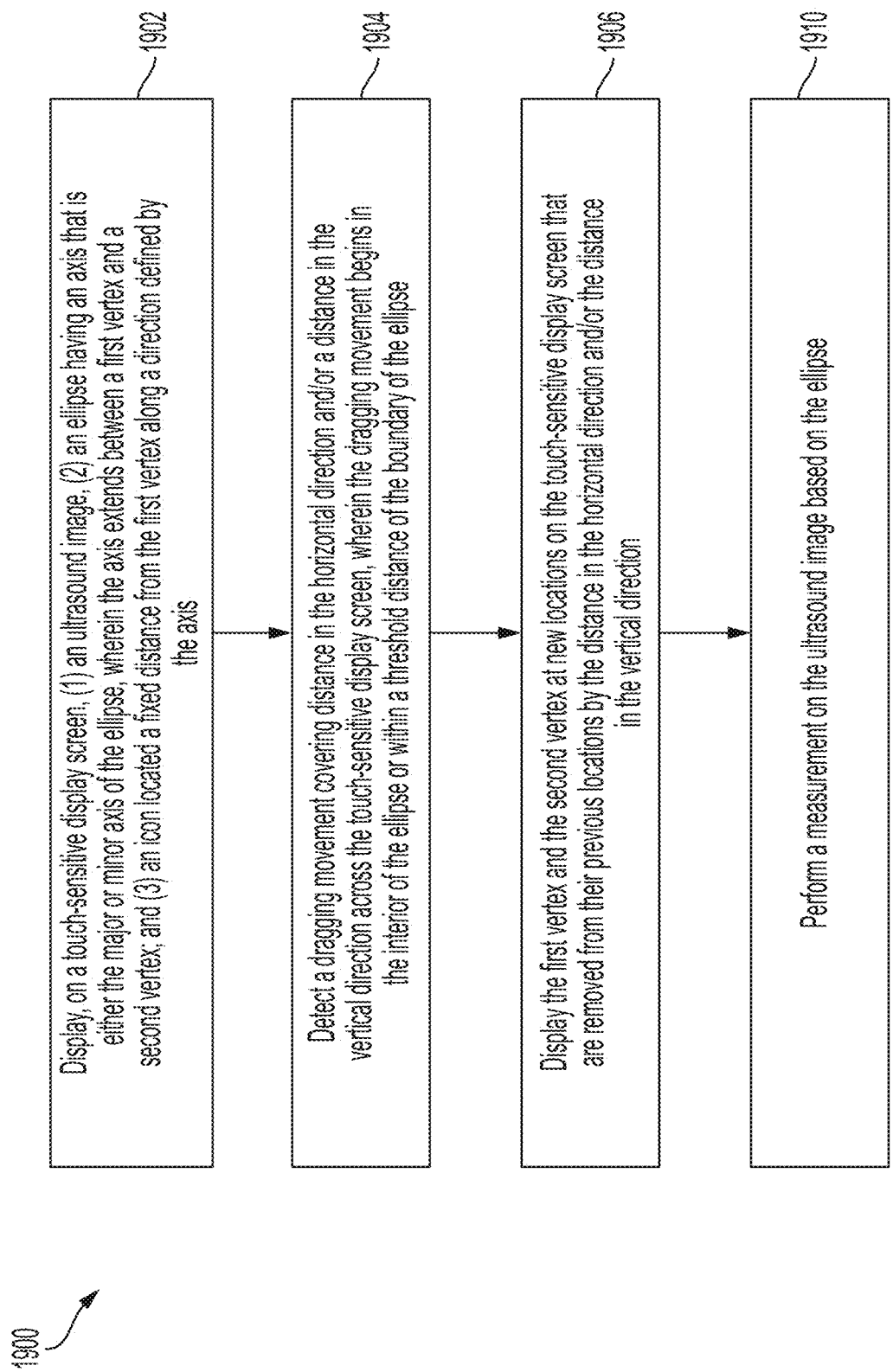
FIG. 19 illustrates an example process for performing measurements on an ultrasound image based on a line, in accordance with certain embodiments described herein.

FIG. 19 illustrates an example process 1900 for performing measurements on an ultrasound image based on an ellipse, in accordance with certain embodiments described herein. Further description of the process 1900 may be found with reference to FIG. 9.

In act 1902, the processing device displays, on a touch-sensitive display screen, (1) an ultrasound image, (2) an ellipse having an axis that is either the major or minor axis of the ellipse, wherein the axis extends between a first vertex and a second vertex; and (3) an icon located a fixed distance from the first vertex along a direction defined by the axis. The process 1900 proceeds from act 1902 to act 1904.

In act 1904, the processing device detects a dragging movement covering distance in the horizontal direction and; or a distance in the vertical direction across the touch-sensitive display screen, where the dragging movement begins in the interior of the ellipse or within a threshold distance of the boundary of the ellipse. The process 1900 proceeds from act 1904 to act 1906.

In act 1906, the processing device displays the first vertex and the second vertex at new locations on the touch-sensitive display screen that are removed from their previous locations by the distance in the horizontal direction and/or the distance in the vertical direction covered by the dragging movement. The process 1900 proceeds from act 1906 to act 1908.

In act 1908, the processing device performs a measurement performed on the ultrasound image based on the ellipse. For example, the processing device may perform a calculation of the spatial length represented by the ultrasound image along the circumference of the ellipse or a calculation of the spatial area represented by the ultrasound image within the ellipse. In some embodiments, the processing device may display the result of the measurement.

In some embodiments, certain acts of the process 1900 may be absent. For example, in some embodiments, act 1910 may be absent. In some embodiments, acts 1904-1910 may be absent. In some embodiments, acts 1904-1908 may be absent. In some embodiments, other combinations of acts may be absent.

The above description has described that a user may modify measurement tools (e.g., a line or an ellipse) through dragging movements that begin on or within a threshold distance of an icon that is located a fixed distance from a portion of the measurement tool. In some embodiments, one or more of the icons described above may be absent, and a user may modify measurement tools through dragging movements that begin on or within a threshold distance of a region of the touch-sensitive display screen that is located the fixed distance from the portion of the measurement tool, even though the region does not contain an icon.

The above description has described modifying measurement tools (e.g., a line or an ellipse) based on a distance in the horizontal and/or vertical direction covered by a dragging movement. In some embodiments, the processing device may modify measurement tools based on taps. In particular, a user may tap an icon and then another location on the touch-sensitive display screen. The processing device may then modify the measurement tool based on the distance in the horizontal and/or vertical direction between the two tapped locations.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Figure 20:
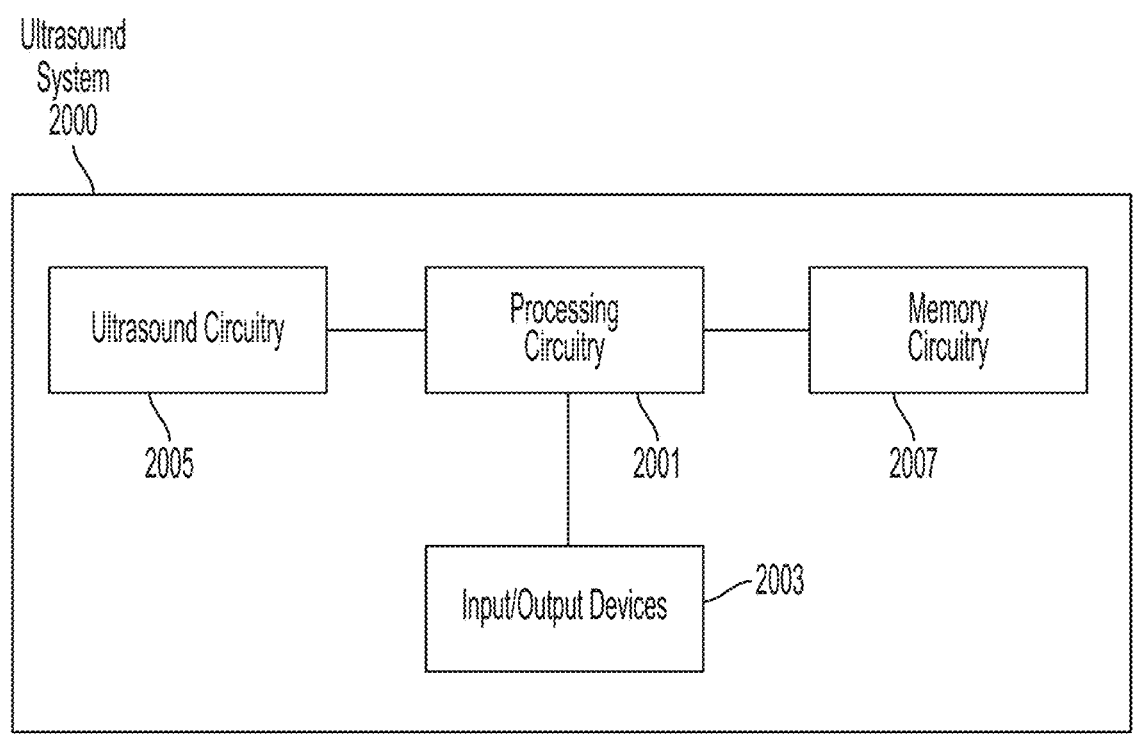
FIG. 20 illustrates a schematic block diagram illustrating aspects of an example ultrasound system upon which various aspects of the technology described herein may be practiced.

FIG. 20 illustrates a schematic block diagram illustrating aspects of an example ultrasound system 2000 upon which various aspects of the technology described herein may be practiced. For example, one or more components of the ultrasound system 2000 may perform any of the processes described herein. As shown, the ultrasound system 2000 includes processing circuitry 2001, input/output devices 2003, ultrasound circuitry 2005, and memory circuitry 2007.

The ultrasound circuitry 2005 may be configured to generate ultrasound data that may be employed to generate an ultrasound image. The ultrasound circuitry 2005 may include one or more ultrasonic transducers monolithically integrated onto a single semiconductor die. The ultrasonic transducers may include, for example, one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 2005 (e.g., transmit circuitry, receive circuitry, control circuitry, power management circuitry, and processing circuitry) to form a monolithic ultrasound imaging device.

The processing circuitry 2001 may be configured to perform any of the functionality described herein. The processing circuitry 2001 may include one or more processors (e.g., computer hardware processors). To perform one or more functions, the processing circuitry 2001 may execute one or more processor-executable instructions stored in the memory circuitry 2007. The memory circuitry 2007 may be used for storing programs and data during operation of the ultrasound system 2000. The memory circuitry 2007 may include one or more storage devices such as non-transitory computer-readable storage media. The processing circuitry 2001 may control writing data to and reading data from the memory circuitry 2007 in any suitable manner.

In some embodiments, the processing circuitry 2001 may include specially-programmed and/or special-purpose hardware such as an application-specific integrated circuit (ASIC). For example, the processing circuitry 2001 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network.

The input/output (I/O) devices 2003 may be configured to facilitate communication with other systems and/or an operator. Example I/O devices 2003 that may facilitate communication with an operator include: a keyboard, a mouse, a trackball, a microphone, a touch-sensitive display screen, a printing device, a display screen, a speaker, and a vibration device. Example I/O devices 2003 that may facilitate communication with other systems include wired and/or wireless communication circuitry such as BLUETOOTH, ZIGBEE, Ethernet, WiFi, and/or USB communication circuitry.

It should be appreciated that the ultrasound system 2000 may be implemented using any number of devices. For example, the components of the ultrasound system 2000 may be integrated into a single device. In another example, the ultrasound circuitry 2005 may be integrated into an ultrasound imaging device that is communicatively coupled with a processing device that includes the processing circuitry 2001, the input/output devices 2003, and the memory circuitry 2007.

Figure 21:
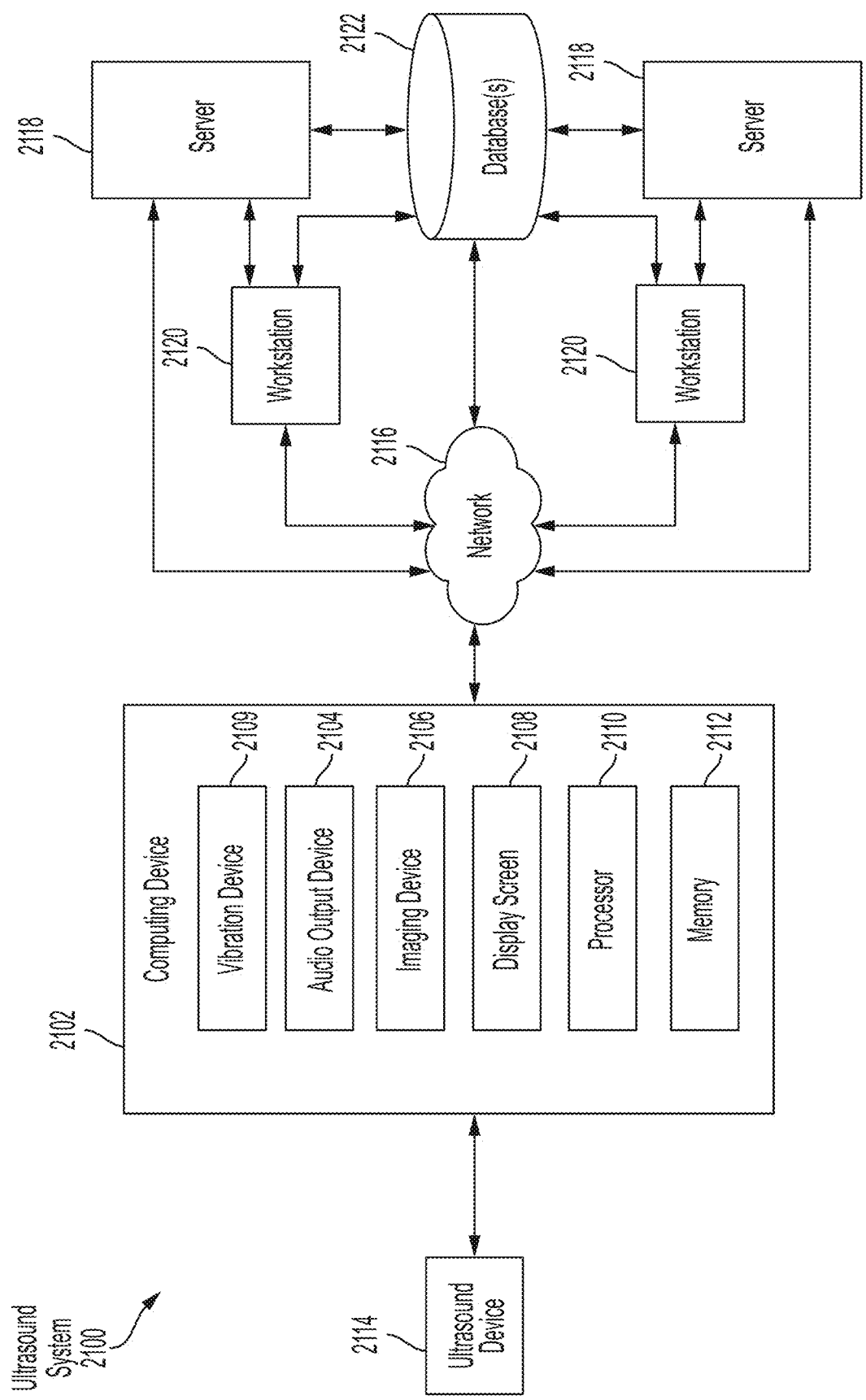
FIG. 21 is a schematic block diagram illustrating aspects of another example ultrasound system upon which various aspects of the technology described herein may be practiced.

FIG. 21 is a schematic block diagram illustrating aspects of another example ultrasound system 2100 upon which various aspects of the technology described herein may be practiced. For example, one or more components of the ultrasound system 2100 may perform any of the processes described herein. As shown, the ultrasound system 2100 includes an ultrasound imaging device 2114 in wired and/or wireless communication with a processing device 2102. The processing device 2102 includes an audio output device 2104, an imaging device 2106, a display screen 2108, a processor 2110, a memory 2112, and a vibration device 2109. The processing device 2102 may communicate with one or more external devices over a network 2116. For example, the processing device 2102 may communicate with one or more workstations 2120, servers 2118, and/or databases 2122.

The ultrasound imaging device 2114 may be configured to generate ultrasound data that may be employed to generate an ultrasound image. The ultrasound imaging device 2114 may be constructed in any of a variety of ways. In some embodiments, the ultrasound imaging device 2114 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data.

The processing device 2102 may be configured to process the ultrasound data from the ultrasound imaging device 2114 to generate ultrasound images for display on the display screen 2108. The processing may be performed by, for example, the processor 2110. The processor 2110 may also be adapted to control the acquisition of ultrasound data with the ultrasound imaging device 2114. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

Additionally (or alternatively), the processing device 2102 may be configured to perform any of the processes described herein (e.g., using the processor 2110). For example, the processing device 2102 may be configured to automatically determine an anatomical feature being imaged and automatically select, based on the anatomical feature being imaged, an ultrasound imaging preset corresponding to the anatomical feature. As shown, the processing device 2102 may include one or more elements that may be used during the performance of such processes. For example, the processing device 2102 may include one or more processors 2110 (e.g., computer hardware processors) and one or more articles of manufacture that include non-transitory computer-readable storage media such as the memory 2112. The processor 2110 may control writing data to and reading data from the memory 2112 in any suitable manner. To perform any of the functionality described herein, the processor 2110 may execute one or more processor-executable instructions stored in one or more non-transitory computer-readable storage media (e.g., the memory 2112), which may serve as non-transitory computer-readable storage media storing processor-executable instructions for execution by the processor 2110.

In some embodiments, the processing device 2102 may include one or more input and/or output devices such as the audio output device 2104, the imaging device 2106, the display screen 2108, and the vibration device 2109. The audio output device 2104 may be a device that is configured to emit audible sound such as a speaker. The imaging device 2106 may be configured to detect light (e.g., visible light) to form an image such as a camera. The display screen 2108 may be configured to display images and/or videos such as a liquid crystal display (LCD), a plasma display, and/or an organic light emitting diode (OLED) display. The display screen 2018 may be a touch-sensitive display screen. The vibration device 2109 may be configured to vibrate one or more components of the processing device 2102 to provide tactile feedback. These input and/or output devices may be communicatively coupled to the processor 2110 and/or under the control of the processor 2110. The processor 2110 may control these devices in accordance with a process being executed by the process 2110 (such as the processes shown in FIGS. 15-19). Similarly, the processor 2110 may control the audio output device 2104 to issue audible instructions and/or control the vibration device 2109 to change an intensity of tactile feedback (e.g., vibration) to issue tactile instructions. Additionally (or alternatively), the processor 2110 may control the imaging device 2106 to capture non-acoustic images of the ultrasound imaging device 2114 being used on a subject to provide an operator of the ultrasound imaging device 2114 an augmented reality interface.

It should be appreciated that the processing device 2102 may be implemented in any of a variety of ways. For example, the processing device 2102 may be implemented as a handheld device such as a mobile smartphone or a tablet. Thereby, an operator of the ultrasound imaging device 2114 may be able to operate the ultrasound imaging device 2114 with one hand and hold the processing device 2102 with another hand. In other examples, the processing device 2102 may be implemented as a portable device that is not a handheld device such as a laptop. In yet other examples, the processing device 2102 may be implemented as a stationary device such as a desktop computer.

In some embodiments, the processing device 2102 may communicate with one or more external devices via the network 2116. The processing device 2102 may be connected to the network 2116 over a wired connection (e.g., via an Ethernet cable) and/or a wireless connection (e.g., over a WiFi network). As shown in FIG. 21, these external devices may include servers 2118, workstations 2120, and/or databases 2122. The processing device 2102 may communicate with these devices to, for example, off-load computationally intensive tasks. For example, the processing device 2102 may send an ultrasound image over the network 2116 to the server 2118 for analysis (e.g., to identify an anatomical feature in the ultrasound) and receive the results of the analysis from the server 2118. Additionally (or alternatively), the processing device 2102 may communicate with these devices to access information that is not available locally and/or update a central information repository. For example, the processing device 2102 may access the medical records of a subject being imaged with the ultrasound imaging device 2114 from a file stored in the database 2122. In this example, the processing device 2102 may also provide one or more captured ultrasound images of the subject to the database 2122 to add to the medical record of the subject. For further description of ultrasound imaging devices and systems, see U.S. Patent Application Publication No. US20170360397A1 titled "UNIVERSAL ULTRASOUND DEVICE AND RELATED APPARATUS AND METHODS."

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment stay be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
   a processing device in operative communication with an ultrasound device, the processing device configured to:
   cause a display on a touch-sensitive display screen of the processing device,
   wherein the display comprises
   an ultrasound image,
   a movable measurement tool including an ellipse having an axis that is either a major axis or a minor axis of the ellipse, wherein the axis extends between a first vertex and a second vertex of the ellipse, and
   an icon that maintains a fixed distance from a portion of the measurement tool, wherein the icon does not overlap the measurement tool and wherein the icon maintains the fixed distance from the first vertex of the ellipse along a direction defined by the axis;
   or the display comprises
   the ultrasound image,
   the moveable measurement tool includes a line extending between a first endpoint and a second endpoint, and
   the icon maintains a fixed distance from a respective one of the first endpoint and second endpoint of the line along a direction defined by the line;
   use the icon to modify the measurement tool;
   wherein, in a case when the measurement tool includes the ellipse, the processing device is further configured to use the icon to modify the measurement tool by controlling a length of the axis of the ellipse that includes the first vertex and to detect a dragging movement covering a distance along the direction defined by the axis of the ellipse across the touch-sensitive display screen, wherein the dragging movement begins on or within a threshold distance of the icon;
   cause a display of the first vertex at a new location on the touch-sensitive display screen that is removed from the first vertex's previous location by the distance along the direction defined by the axis of the ellipse;
   cause a display of the second vertex at a new location on the touch-sensitive display screen that is removed from the second vertex's previous location by the distance along the direction defined by the axis of the ellipse;
   cause a display of the icon at a new location on the touch-sensitive display screen that is removed from the first vertex's new location by the fixed distance along the direction defined by the axis of the ellipse; and
   perform a measurement on the ultrasound image based on the ellipse;
   or
   wherein, in a case when the measurement tool includes the line, the processing device is further configured to: use the icon to modify the measurement tool by controlling a position of the first endpoint of the line and to detect a dragging movement covering a distance in a horizontal direction and/or a distance in a vertical direction across the touch-sensitive display screen, wherein the dragging movement begins on or within a threshold distance of the icon;
   cause a display of the first endpoint at a new location on the touch-sensitive display screen that is removed from the first endpoint's previous location by the distance in the horizontal direction and/or the distance in the vertical direction;
   cause a display of the icon at a new location on the touch-sensitive display screen that is removed from the new location of the first endpoint by the fixed distance along the direction defined by the line; and
   perform a measurement on the ultrasound image based on the line.

2. The apparatus of claim 1, wherein, in the case when the measurement tool includes the ellipse,
   the processing device is further configured to modify the icon to control a rotation of the ellipse by detecting a dragging movement covering a distance orthogonal to the direction defined by the axis of the ellipse across the touch-sensitive display screen, wherein the dragging movement begins on or within a threshold distance of the icon; and
   display the first vertex and the second vertex at new locations on the touch-sensitive display screen that are rotated from their previous locations based on the distance that is along and/or the distance that is orthogonal to the direction defined by the axis of the ellipse.

3. The apparatus of claim 1, wherein, in the case when the measurement tool includes the ellipse, the processing device is further configured to:
   detect a dragging movement covering a distance in a horizontal direction and/or a vertical direction across the touch-sensitive display screen, wherein the dragging movement begins in an interior of the ellipse or within a threshold distance of a boundary of the ellipse; and
   display the first vertex and the second vertex at new locations on the touch-sensitive display screen that are removed from their previous locations by the distance in the horizontal direction and/or the distance in the vertical direction.

4. The apparatus of claim 1, wherein the measurement tool overlays the ultrasound image.

5. The apparatus of claim 1, wherein the icon comprises a circle.

6. The method of claim 1, wherein the processor is configured to perform a measurement comprising a calculation of a spatial length represented by an ultrasound image along a circumference of the ellipse of the movable measurement tool.

7. The method of claim 1, wherein the processor is configured to perform a measurement comprising a calculation of a spatial area represented by an ultrasound image bounded within a circumference of the ellipse of the movable measurement tool.

8. The method of claim 1, wherein the processor is configured to perform a measurement and display a result of the measurement on the touch-sensitive display screen.

9. A method, comprising:
   displaying on a touch-sensitive display screen of a processing device in operative communication with an ultrasound device,
      wherein the display comprises
         an ultrasound image,
         a movable measurement tool that includes an ellipse having an axis that is either a major axis or a minor axis of the ellipse, wherein the axis extends between a first vertex and a second vertex of the ellipse, and
         an icon that maintains a fixed distance from a portion of the measurement to wherein the icon does not overlap the measurement tool; and wherein the icon maintains the fixed distance from the first vertex of the ellipse along a direction defined by the axis,
      or the display comprises
         the ultrasound image,
         the moveable measurement tool that includes a line extending between a first endpoint and a second endpoint, and
         the icon that maintains a fixed distance from a respective one of the first endpoint and second endpoint of the line along a direction defined by the line;
   in a case when the measurement tool includes the ellipse, using the icon to modify the measurement tool by controlling a length of the axis of the ellipse that includes the first vertex and to detect a dragging movement covering a distance along the direction defined by the axis of the ellipse across the touch-sensitive display screen, wherein the dragging movement begins on or within a threshold distance of the icon;
   displaying the first vertex at a new location on the touch-sensitive display screen that is removed from the first vertex's previous location by the distance along the direction defined by the axis of the ellipse;
   displaying the second vertex at a new location on the touch-sensitive display screen that is removed from the second vertex's previous location by the distance along the direction defined by the axis of the ellipse; and
   displaying the icon at a new location on the touch-sensitive display screen that is removed from the first vertex's new location by the fixed distance along the direction defined by the axis of the ellipse; and
   performing a measurement on the ultrasound image based on the ellipse;
   or
   in a case when the measurement tool includes the line, using the icon to modify the measurement tool by controlling the position of the first endpoint of the line and to detect a dragging movement covering a distance in a horizontal direction and/or a distance in a vertical direction across the touch-sensitive display screen, wherein the dragging movement begins on or within a threshold distance of the icon;
   displaying the first endpoint at a new location on the touch-sensitive display screen that is removed from the first endpoint's previous location by the distance in the horizontal direction and/or the distance in the vertical direction;
   displaying the icon at a new location on the touch-sensitive display screen that is removed from the new location of the first endpoint or second endpoint by the fixed distance along the direction defined by the line; and
   performing a measurement on the ultrasound image based on the line.

10. The method of claim 9, further comprising,
    in the case when the measurement tool includes the ellipse, modifying the icon to control a rotation of the ellipse by detecting a dragging movement covering a distance orthogonal to the direction defined by the axis of the ellipse across the touch-sensitive display screen, wherein the dragging movement begins on or within a threshold distance of the icon; and
    displaying the first vertex and the second vertex at new locations on the touch-sensitive display screen that are rotated from their previous locations based on the distance that is along and/or the distance that is orthogonal to the direction defined by the axis of the ellipse.

11. The method of claim 9, further comprising:
    in the case when the measurement tool includes the ellipse, detecting a dragging movement covering a distance in a horizontal direction and/or a vertical direction across the touch-sensitive display screen, wherein the dragging movement begins in an interior of the ellipse or within a threshold distance of a boundary of the ellipse; and
    displaying the first vertex and the second vertex at new locations on the touch-sensitive display screen that are removed from their previous locations by the distance in the horizontal direction and/or the distance in the vertical direction.

12. The method of claim 9, wherein the measurement tool overlays the ultrasound image.

13. The method of claim 9, wherein the icon comprises a circle.

* * * * *